US006307943B1

(12) United States Patent
Yamagishi

(10) Patent No.: US 6,307,943 B1
(45) Date of Patent: Oct. 23, 2001

(54) ELECTRO-ACOUSTIC TRANSDUCER AND HOUSING

(75) Inventor: Makoto Yamagishi, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 08/320,935

(22) Filed: Oct. 11, 1994

Related U.S. Application Data

(63) Continuation of application No. 07/588,030, filed on Sep. 24, 1990, now abandoned.

(30) Foreign Application Priority Data

Sep. 30, 1989 (JP) ..................................................... 1-255797

(51) Int. Cl.[7] ................................ H04R 1/02; A61B 7/02

(52) U.S. Cl. ........................... 381/312; 381/322; 181/132

(58) Field of Search ..................................... 181/129, 132; 379/431; 381/62, 68, 68.6, 154, 185, 186, 187, 312, 322

(56) References Cited

U.S. PATENT DOCUMENTS

| | | | | |
|---|---|---|---|---|
| 3,667,569 | * | 6/1972 | Mackey et al. | 381/187 |
| 3,816,678 | * | 6/1974 | Gefvert et al. | 381/185 |
| 3,995,113 | | 11/1976 | Tani | 381/154 |
| 4,291,203 | * | 9/1981 | Bellafiore | 381/68 |
| 4,381,830 | * | 5/1983 | Jelonek et al. | 181/129 |
| 4,467,145 | * | 8/1984 | Borstel | 381/68 |
| 4,864,610 | * | 9/1989 | Stevens | 379/431 |
| 4,972,492 | * | 11/1990 | Tanaka et al. | 381/187 |
| 4,981,194 | * | 1/1991 | Kamon et al. | 181/129 |
| 5,022,486 | * | 6/1991 | Miura et al. | 181/132 |
| 5,031,219 | * | 7/1991 | Ward et al. | 381/68.6 |
| 5,142,587 | * | 8/1992 | Kobayashi | 381/187 |

FOREIGN PATENT DOCUMENTS

| | | | | |
|---|---|---|---|---|
| 3210034 | * | 9/1982 | (DE) . | |
| 0158391 | * | 10/1985 | (EP) | 381/68.7 |
| 0314419 | | 5/1989 | (EP) | 381/154 |
| 2558055 | * | 7/1985 | (FR) | 381/68.7 |
| 2604589 | | 9/1987 | (FR) | 381/154 |
| 2599922 | | 12/1987 | (FR) | 381/154 |
| 2078057 | | 12/1981 | (GB) | 381/154 |
| 2079099 | * | 1/1982 | (GB) | 381/187 |
| 2204759 | * | 11/1988 | (GB) | 381/68 |

OTHER PUBLICATIONS

United Hearing Systems, Incorporated "In the Ear and Intra Canal" Aug., 1990.*

ACS Communications, Incorporated "ACS Telephone Headsets" Aug., 1990.*

ACS Communications, Incorporated "Noise Cancelling Headsets", Oct. 1, 1990.*

* cited by examiner

*Primary Examiner*—William Cumming
(74) *Attorney, Agent, or Firm*—Ronald P. Kananen; Rader, Fishman & Grauer

(57) ABSTRACT

An electro-acoustic transducer for a sound reproducing system includes an electro-acoustic transducer in a cabinet and a sound guide tube for conducting the sound from the transducer unit out of the cabinet. The sound guide tube has a sound radiating end with a smaller diameter than the external acoustic meatus to allow the sound radiating end to be inserted into the external auditory meatus.

22 Claims, 17 Drawing Sheets

ELECTRO-ACOUSTIC TRANSDUCER AND HOUSING

This application is a continuation of application Ser. No. 07/588,030 filed Sep. 24, 1990 now abandoned.

BACKGROUND OF THE INVENTION

1. Field of the Invention

This invention relates to an electro-acoustic transducer for sound reproduction and a sound reproducing system constructed with the use of the electro-acoustic transformer.

2. Description of the Related Art

Up to now, there is proposed an electro-acoustic transducer or a sound reproducing system supplied with acoustic signals in the form of electrical signals and adapted for converting the electrical signals into sound to realize sound reproduction, such as a headphone device or an earphone device.

The aforementioned electro-acoustic transducer comprises an electro-acoustic transducer unit for converting the acoustic signals into sound. The electro-acoustic transducer when constructed as the headphone device is adapted for supporting a pair of electro-acoustic transducer units in opposition to both auricles of the user.

The sound reproducing system also includes a pair of speaker units as the sound reproducing device arranged for converting the sound signals into sound. The speaker unit includes a speaker unit having a diaphragm and functioning as the sound reproducing unit. A speaker cabinet accommodates the speaker unit with the sound radiating side facing to outside. With the present sound reproducing system, the speaker device is arranged in front of and faces the listener to effect sound reproduction by the speaker device.

Meanwhile, with the above described electro-acoustic transducer, constructed as the headphone device, the electroacoustic transducer unit constituting the transducer faces the listener's tympanic membrane, so that standing waves are produced between the transducer unit and the tympanic membrane. The listener using such electro-acoustic transducer feels oppressed due to the standing waves or feels as if the sound source were within his head.

With the above described electro-acoustic transducer, the electro-acoustic transducer unit is supported for substantially closing the listener's external auditory meatus so that the listener using the electro-acoustic transducer feels unable to hear the external sound. Thus the use of the electro-acoustic transducer during walking on the road or driving a vehicle or car endangers safe walking or driving since the user can hardly recognize the outside situation.

With the above sound reproducing system, for optimum sound reproduction over a wide frequency range including the lower frequency range, it becomes necessary to increase the volume of the speaker cabinet constituting the speaker device or to increase the area of the diaphragm of the speaker unit. If the cabinet volume or diaphragm area is increased, the size of the apparatus increases.

On the other hand, with a sound reproducing system in which the size of the apparatus is increased to enable sound reproduction over a wide frequency range, it may be occasionally impossible to effect sound reproduction at a sufficient sound pressure in view of the inconveniences to the neighbors under the straitened or congested housing circumstances.

OBJECT AND SUMMARY OF THE INVENTION

In view of the foregoing, it is a principal object of the present invention to provide an electro-acoustic transducer which, when arranged as a headphone device or an earphone device, does not give rise to oppressed feeling or a feeling as if the sound source were within the user's head.

It is another object of the present invention to provide a sound reproducing system which is capable of satisfactorily reproducing the sound over a wide frequency range including the low frequency range without unnecessary increasing the size of the system or inconvenience to the neighbors.

In accordance with the present invention, there is provided an electro-acoustic transducer comprising an electro-acoustic transducer accommodated in a cabinet, and a sound guide tube for conducting the sound from the electro-acoustic transducer unit out of said cabinet, said sound guide tube having at least the sound radiating end with a diameter smaller than the external acoustic meatus to allow said sound radiating end to be introduced into the external auditory meatus.

In accordance with the present invention, there is also provided a sound reproducing system comprising a sound reproducing apparatus supplied with acoustic signals, and an electro-acoustic transducer including an electro-acoustic transducer unit accommodate in a cabinet, and a sound guide tube for conducting the sound from the electro-acoustic transducer unit out of said cabinet, said sound guide tube having at least the sound radiating end with a diameter smaller than the external auditory meatus to permit said sound radiating end to be introduced into the external auditory meatus, said electroacoustic transducer being adapted for reproducing at least the low-frequency component of the acoustic signal of the frequency range reproduced by said sound reproducing apparatus.

With the electro-acoustic transducer of the present invention, the sound guide tube adapted for conducting the sound radiated from the electro-acoustic transducer unit accommodated in the cabinet towards the outside of the cabinet has at least its sound radiating end with a diameter smaller than the external auditory meatus so that the sound radiating end may be inserted into the external auditory meatus. Thus the sound may be conducted into the inside of the external auditory meatus without stopping the external auditory meatus.

The sound reproducing system according to the present invention is so arranged and conducted that the sound may be reproduced by the sound reproducing apparatus adapted for being supplied with acoustic signals and for converting the acoustic signals into sound for reproduction thereof, and that the electro-acoustic transducer adapted for converting at least the low-frequency component of the acoustic signals supplied to said sound reproducing apparatus conducts the sound radiated from the electro-acoustic transducer unit accommodated in the cabinet towards the outside of the unit, while radiating the sound into the external acoustic meatus by way of a sound guide tube having at least its sound radiating end with a diameter smaller than the external auditory meatus to permit the sound radiating end to be inserted into the external auditory meatus without stopping the external auditory meatus. In this manner, both the sound reproduced by the sound reproducing apparatus and the sound reproduced by the electro-acoustic transducer unit of the electro-acoustic transducer may be heard simultaneously.

DETAILED DESCRIPTION OF PREFERRED EMBODIMENTS

Figure 1:
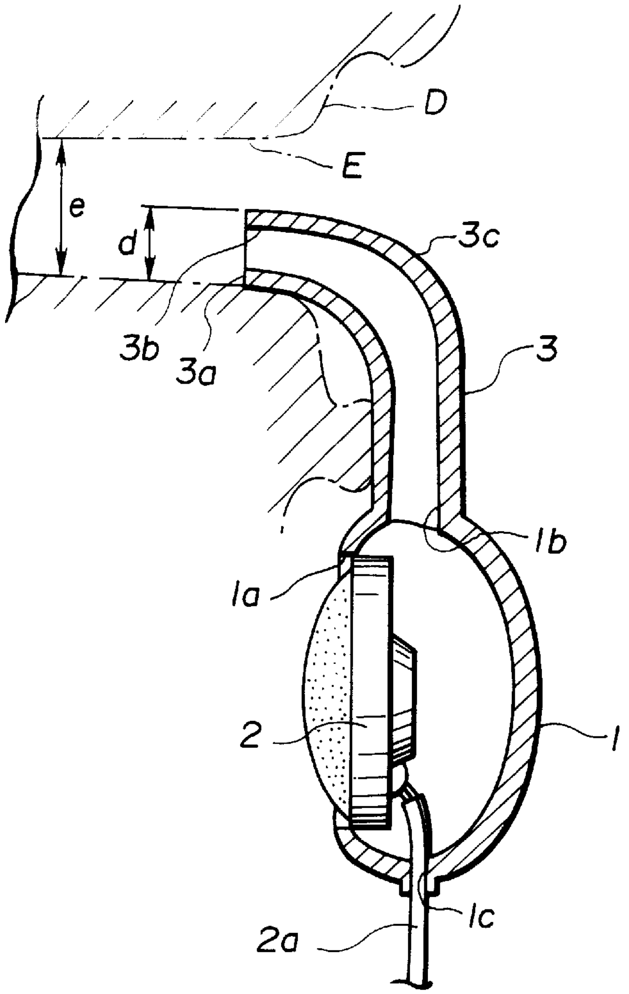
FIG. 1 is a diagrammatic cross-sectional view showing the construction of the electro-acoustic transducer of the present invention.

By referring to the drawings, certain preferred embodiments of the present invention will be explained in detail.

FIGS. 1 to 4 illustrate an embodiment of an electroacoustic transducer which is constructed as an earphone device attached to auricles.

The earphone device shown in FIG. 1 includes a cabinet 1 and a sound reproducing unit 2 which is an electro-acoustic transducer unit housed within the cabinet 1.

The sound reproducing unit 2 includes a diaphragm and a magnetic circuit. A voice coil is mounted on the diaphragm so as to lie in the magnetic path of the magnetic circuit. That is, with the present sound reproducing unit 2, when the sound signal which is the driving signal is supplied to the voice coil via feeder 2*a*, the voice coil is driven and offset in the magnetic path of the magnetic circuit. The offsetting of the voice coil is transmitted to the diaphragm which then radiates the reproduced sound towards the front and rear sides.

The cabinet 1 is formed of synthetic resin, for example, and is formed for accommodating and supporting the sound reproducing unit 2. The cabinet 1 has an opening 1*a* whereby the front side functions as the sound radiating side of the sound reproducing unit 2 is caused to face to outside. The cabinet 1 accommodates and supports the sound reproducing unit 2 with the front side of the sound reproducing unit 2 facing outwards via opening 1*a*.

The feeder 2*a* is led out of the cabinet 1 by means of a feeder outlet 1*c* provided in the cabinet 1.

The cabinet 1 is provides with a sound guide tube 3 establishing communication between the inside and the outside of the cabinet 1. Thus the cabinet 1 is provided with a sound conducting opening 1*b* situated at the lateral side of the sound reproducing unit 2, the sound guide tube 3 in the form of a hollow cylinder is provided in alignment with the opening 1*b*. This sound guide tube 3 is formed integrally with the cabinet 1 with a predetermined length so as to be projected out of the cabinet 1. The terminal end 3*a*, functioning as the sound radiating end, is opened as the sound radiating opening 3*b*.

Thus the sound radiated from the rear side of the sound reproducing unit 2 into the inside of the cabinet 1 is propagated from the inside of the cabinet by way of the sound conducting opening 1*b* into the inside of the sound guide tube 3 so as to be radiated outwards via sound radiating opening 3*b* of the sound guide tube 3.

The distal end 3*a* of the sound guide tube 3 has an outside diameter, as shown by arrow d in FIG. 1, which is smaller than the inside diameter of the external auditory meatus E shown by arrow e in FIG. 1. The distal end 3*a* may be inserted into the external auditory meatus E without stopping the external auditory meatus E to provide an interstice large enough to permit sound propagation between it and the inner wall of the external auditory meatus E. The inside diameter of the external auditory meatus E of a human is usually 7 to 9 mm. The sound guide tube 3 has its distal portion 3*c* bent arcuately in about a 90° direction. Thus, the sound radiating opening 3*b* is directed to the inside of the external auditory meatus E.

When the above described earphone device is in use, the distal end 3*a* of the sound guide tube 3 is inserted into the external auditory meatus E, as shown in FIG. 1. The earphone device is supported by a supporting member, as later described. The sound radiated from the sound radiating opening 3*b* at the distal end 3*a* of the sound guide tube inserted into the external auditory meatus E will reach the tympanic membrane, not shown, after propagation through the inside of the external auditory meatus E.

This earphone device allows the sound from the sound reproducing unit 2 to reach the tympanic membrane via the external auditory meatus E without stopping the external auditory meatus E. Hence, with the present earphone device, the sound may be reproduced without impeding the hearing of the external sounds.

Figure 2:
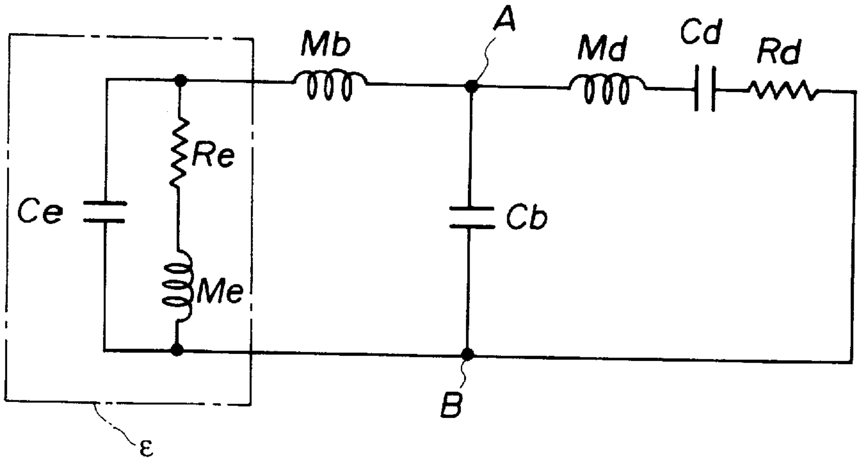
FIG. 2 is an equivalent acoustic circuit diagram showing acoustic characteristics of the electro-acoustic transducer.

FIG. 2 shows an equivalent acoustic circuit showing acoustic characteristics of the earphone device. An equivalent mass Md for the sound reproducing unit 2, a compliance Cd and an acoustic resistance Rd are connected in series and a compliance Cb within the cabinet 1 is connected to the series of the equivalent means Md, compliance Cd and the acoustic resistance Rd to form a closed loop. One of the junctions A between the compliance Cb and the equivalent mass Md, compliance Cd and the acoustic resistance Rd, is connected to an acoustic circuit $\epsilon$ within the external acoustic meatus E via an equivalent mass Mb of the air in the sound guide tube 3. The other junction B between the compliance Cb and the equivalent mass Md, acoustic resistance Rd and compliance Cd is connected directly to the acoustic circuit $\epsilon$ of the external acoustic meatus E. The acoustic circuit $\epsilon$ in the external acoustic meatus E forms a closed loop consisting of the equivalent mass Me within the external auditory meatus E, compliance Ce and acoustic resistance Re. The junction between the compliance Ce and the acoustic resistance Re is connected to an equivalent mass Mb of the air in the sound guide tube 3. The junction between the compliance Ce and the equivalent mass Me is connected to the other junction B between equivalent mass Md, compliance Cd and acoustic resistance Rd and compliance Cb.

With the above acoustic circuit, the resonant frequency $f_0$ of the earphone device $f_0$ is given by $$f_0=1/(2\pi\sqrt{(Md+Mb)}Cd \quad (1)$$

which is lower than the resonance frequency of the sound reproducing unit 2 alone. Hence, with the above earphone device, optimum sound reproduction may be achieved over a wide frequency range including the low frequency range.

Figure 3:
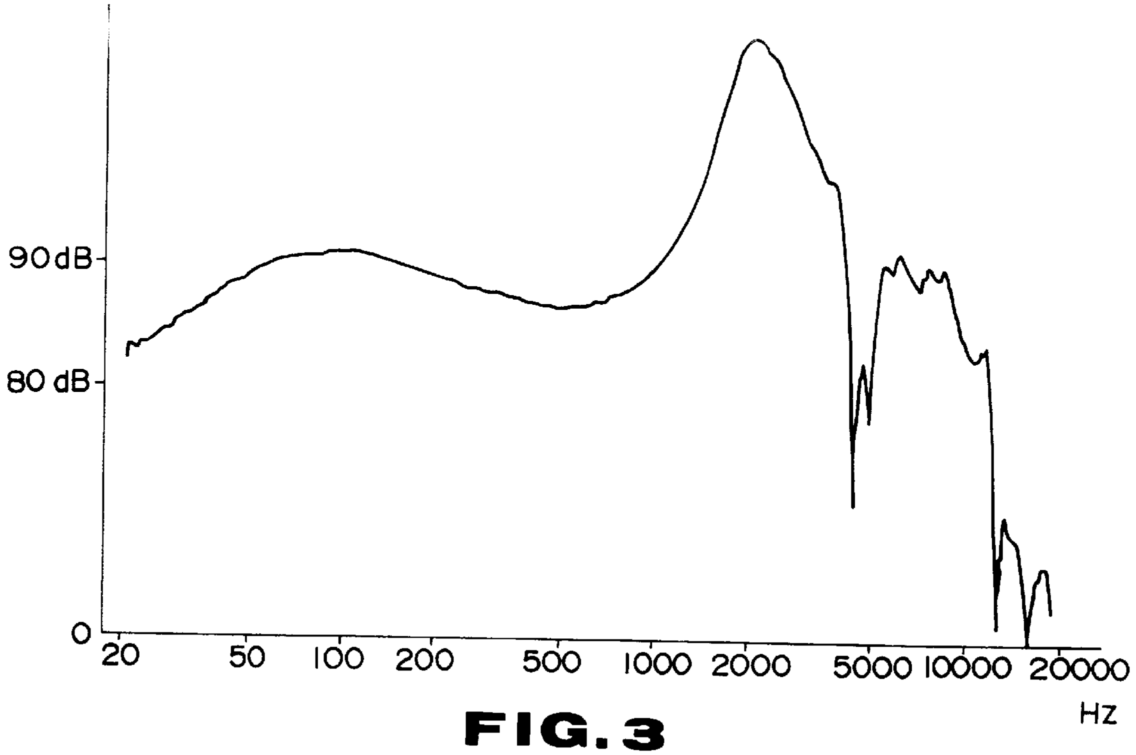
FIG. 3 is a chart showing frequency characteristics of the reproduced sound of the electro-acoustic transducer.
Figure 4:
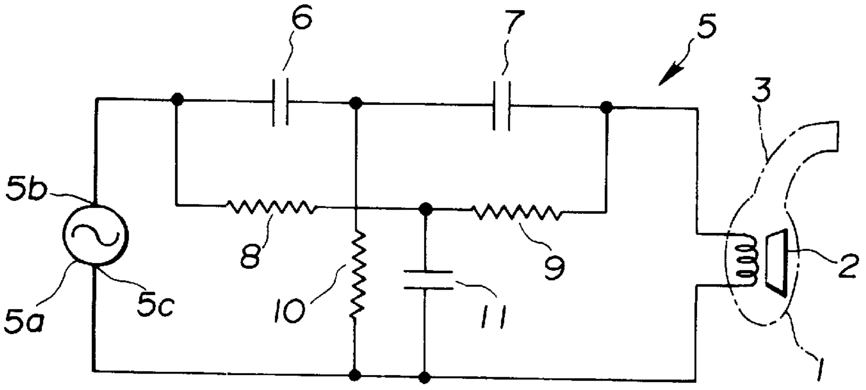
FIG. 4 is a circuit diagram showing the construction of a correction circuit for correcting the frequency characteristics of the electro-acoustic transducer.

Meanwhile, the frequency response of the reproduced sound by the sound reproducing unit 2 alone exhibits a resonance peak at about 2 kHz, as shown in FIG. 3. For reducing the effects of the resonance peak, the above sound signals are supplied via a correction circuit 5 to the sound reproducing unit 2. As shown in FIG. 4, this correction circuit 5 has a series circuit of first and second capacitors 6 and 7 between one of the output ends SD of the signal source 5*a* and the one input end of the sound reproducing unit 2. First and second resistances 8 and 9 are connected in series so as to be in parallel with the capacitors 6 and 7. A point between the capacitors 6 and 7 is connected via third resistor 10 to the other output end 5*c* of the signal source 5*a* which is connected to the other input end of the sound reproducing unit 2. A point between the first resistor 8 and the second resistor 9 is connected via third capacitor 11 to the other output end 5*c* of the signal source 5*a*.

By supplying the above acoustic signals by way of the above described correction circuit 5 to the sound reproducing unit 2, the sound may be reproduced with the frequency characteristics affected less by the resonance peaks.

The electro-acoustic transducer of the present invention may be constructed so that a pair of the above described earphone devices are adapted to be attached to the user's auricles and are used for left and right ears to perform stereophonic sound reproduction.

On the other hand, the sound reproducing unit of the electro-acoustic transducer of the present invention may be accommodated in and supported by the cabinet 1 with the rear side facing outwards by way of the opening 1*a* and the front side facing the inner side of the cabinet 1. In this case, the sound radiated from the front side of the sound reproducing unit 2 may be guided by the sound guide tube 3 to reach the external auditory meatus E.

Construction of Supporting Member Supporting ElectroAcoustic Transducer

Figure 5A:
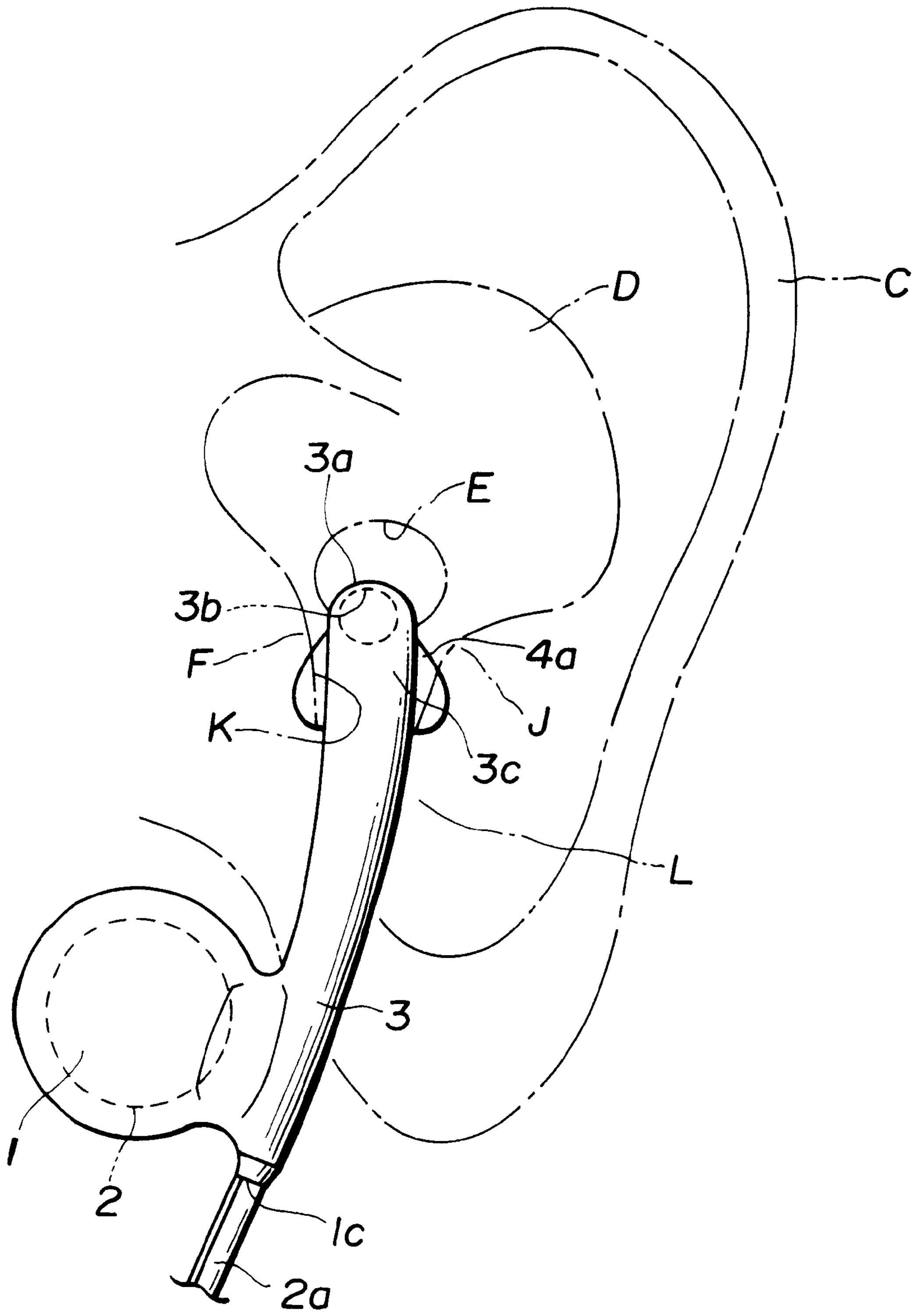
FIG. 5A is a side view showing the state in which the electro-acoustic transducer arranged as an earphone device is attached to user's auricles.
Figure 5B:
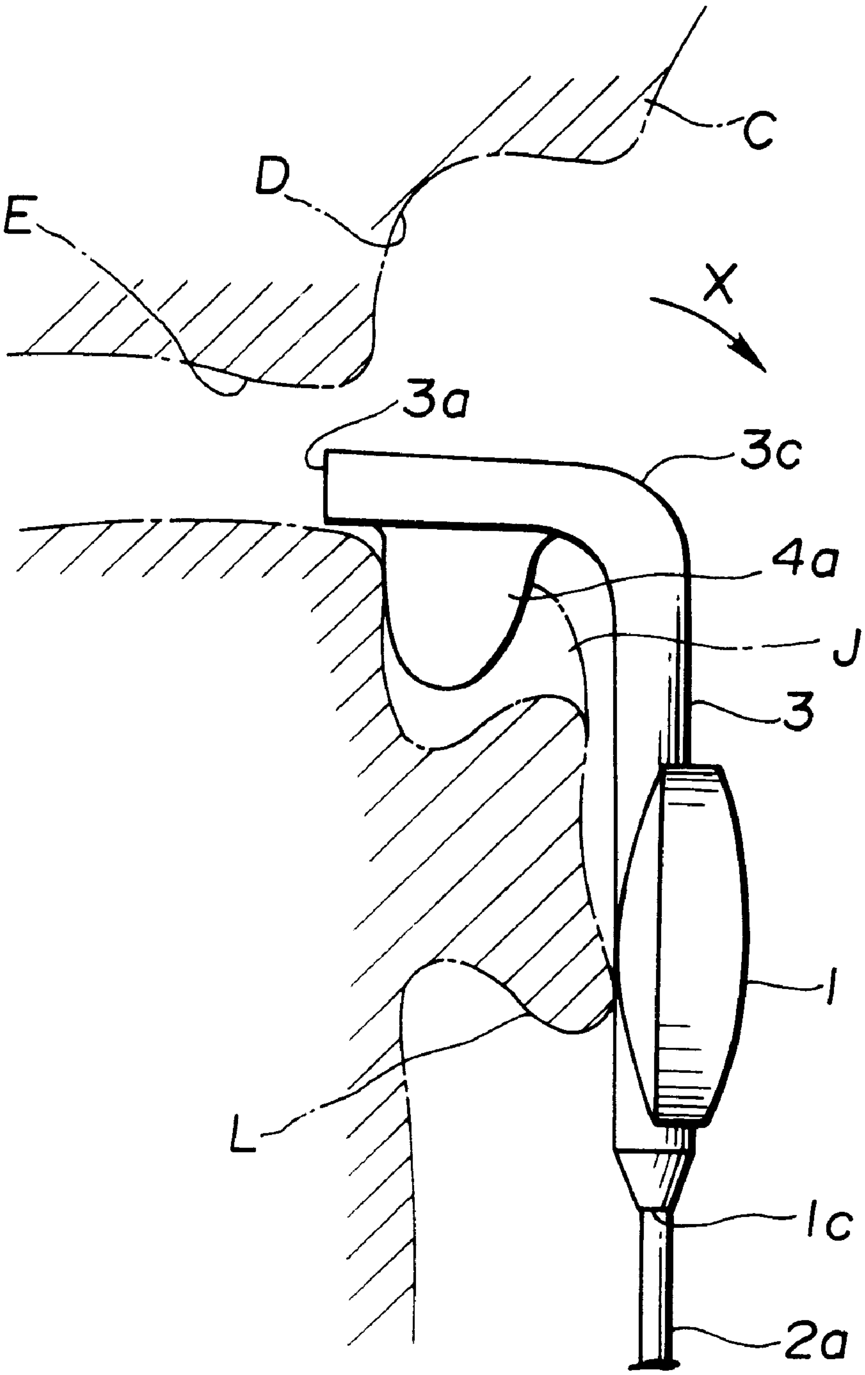
FIG. 5B is a cross-sectional view showing the state in which the electro-acoustic transducer arranged as the earphone device is attached to user's auricles.

The electro-acoustic transducer of the present invention, formed as an earphone device attached to user's auricles when in use, may also be so arranged and constructed as shown in FIGS. 5A and 5B. A protuberance 4*a* is provided as the supporting member at the foremost part 3*c* of the sound guide tube 3. The forward side 3*c* of the sound guide tube 3 is supported in a cavity of the D which is a recessed part of the auricle C. With the present earphone device, when the distal side 3*c* of the sound guide tube 3 is inserted into the cavity of the concha 0, with the proximal side of the ear guide tube 3 directing downwards, the projection 4*a* is supported in abutment with the tragus F and the antitragus J in the lower region of the auricular recess D. The sound guide tube 3 lies in an intertragic notch K between the tragus F and the antitragus J, and is supported in abutment with the outer the outer surface of the otorrhea, a portion of the auricle C, at a position below the intertragic notch K.

With the projection 4*a* supported in abutment with the tragus F and the antitragus J, and with the sound guide tube 3 supported in abutment with the otorrhea L, the distal side 3*c* of the sound guide tube 3 is held within the cavity of the concha D, and the distal end 3*a* of the sound guide tube 3 is introduced into the external auditory meatus E, as shown in FIG. 50. Since the point of abutment of the sound guide tube 3 by the otorrhea L is below the support point for the projection 4*a*, rotation in the direction shown by arrow x in FIG. 5B is inhibited. This guarantee safe and positive support of the earphone device by the auricle C.

Figure 6A:
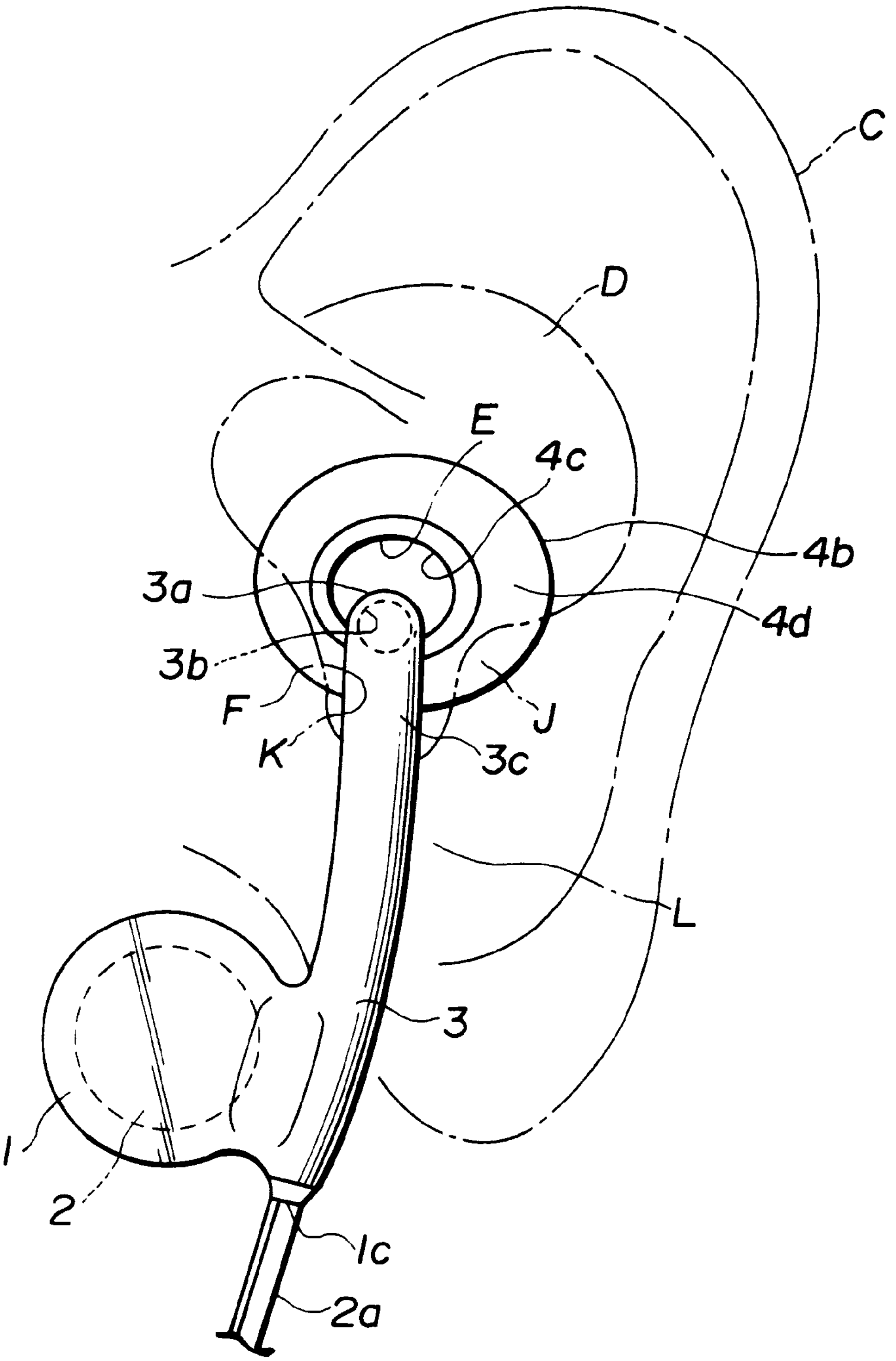
FIG. 6A is a side view showing another example of the state in which the electro-acoustic transducer arranged as the earphone device is attached to user's auricles.
Figure 6B:
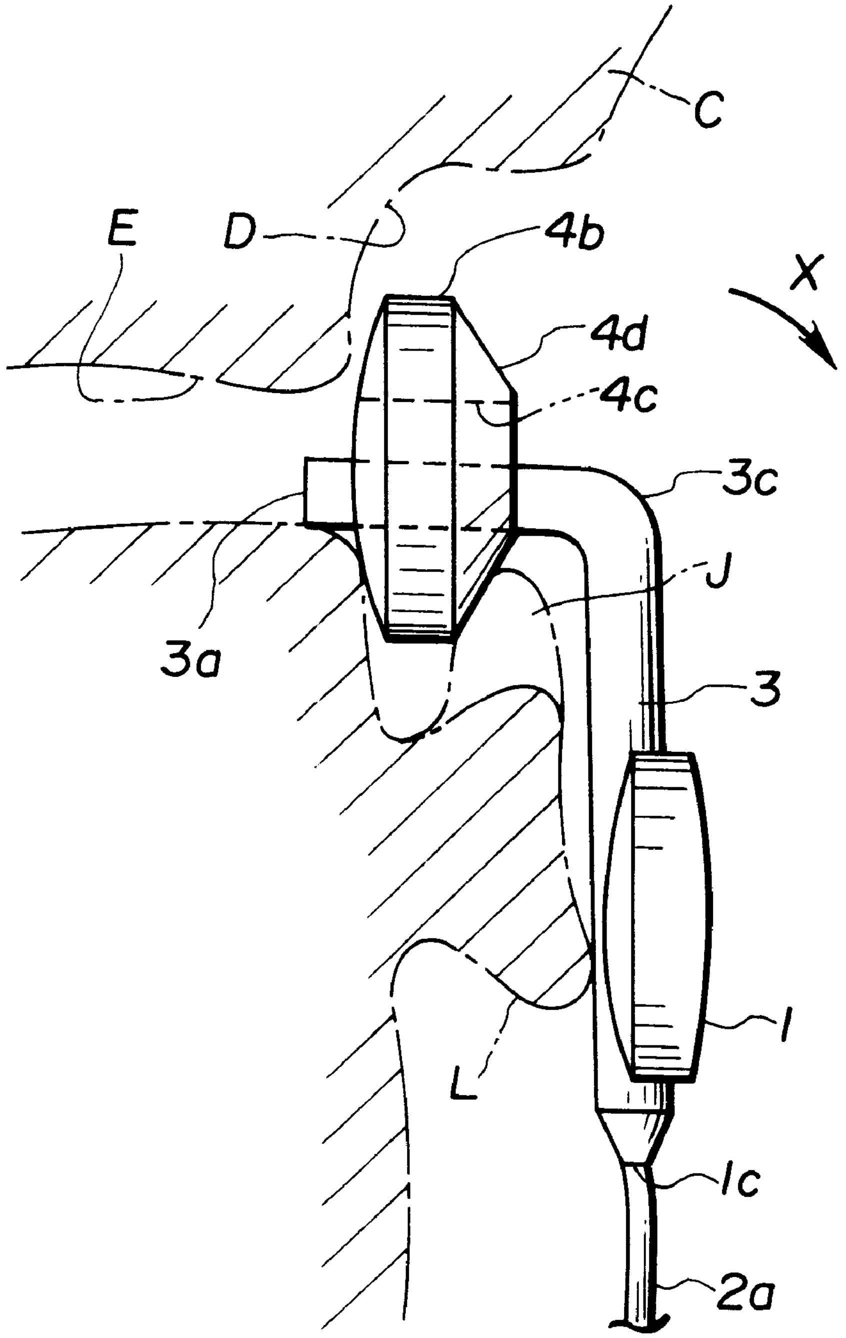
FIG. 6B is a cross-sectional view showing another example of the state in which the electro-acoustic transducer arranged as the earphone device is attached to user's auricles.

A torroidal member 4*b* may also be provided as the supporting member at the distal side 3*c* of the sound guide tube 3, as shown in FIGS. 6A and 6B. The distal side 3*c* of the sound guide tube 3 may be maintained in the cavity of the concha D by the toroidal supporting member 4*b*. When the distal side 3*c* of the sound guide tube 3 is inserted into the cavity of the concha 0, with the proximal side of the round guide tube 3 directing downwards, the torroidal member 4*b* is supported in abutment with the tragus and the antitragus J in the cavity of the concha D. The rear peripheral surface of the torroidal member 4*b*, facing the outside of the auricle C is formed as a tapered inclined portion 4*d* to assure optimum abutment by the tragus F and the antitragus J. The sound guide tube 3 is adapted to hang downwards via the intertragic notch K between the tragus F and the antitragus J and is supported in abutment with the outer lateral surface of the otorrhea L.

When the torroidal member 4*b* is thus supported in abutment with the tragus F and the antitragus, J and the sound guide tube 3 is supported in abutment with the otorrhea L, the distal side 3*c* of the sound guide tube 3 is held within the cavity of the concha D, as shown in FIG. 6B. The distal end 3*a* of the sound guide tube 3 is inserted into the external auditory meatus E, which simultaneously faces outwards by way of a central throughhole 4*c* in the torroidal member 4*b*. Similarly to the earphone device shown in FIG. 5B, the abutting point of the sound guide tube 3 on the otorrhea L and that of the torroidal member 4*b* on the tragus F and the antitragus J act to inhibit rotation of the torroidal member 4*b* in the direction of an arrow x in FIG. 6B. This guarantees safe and positive holding of the earphone device by the auricle C.

With the earphone device shown in FIGS. 5A, 5B, 6A and 6B, the sound tube 3 is adapted to communicate with the cabinet 1 at the lateral surface on the proximal side. The feeder outlet 1*c* is provided on the proximal side.

Figure 7:
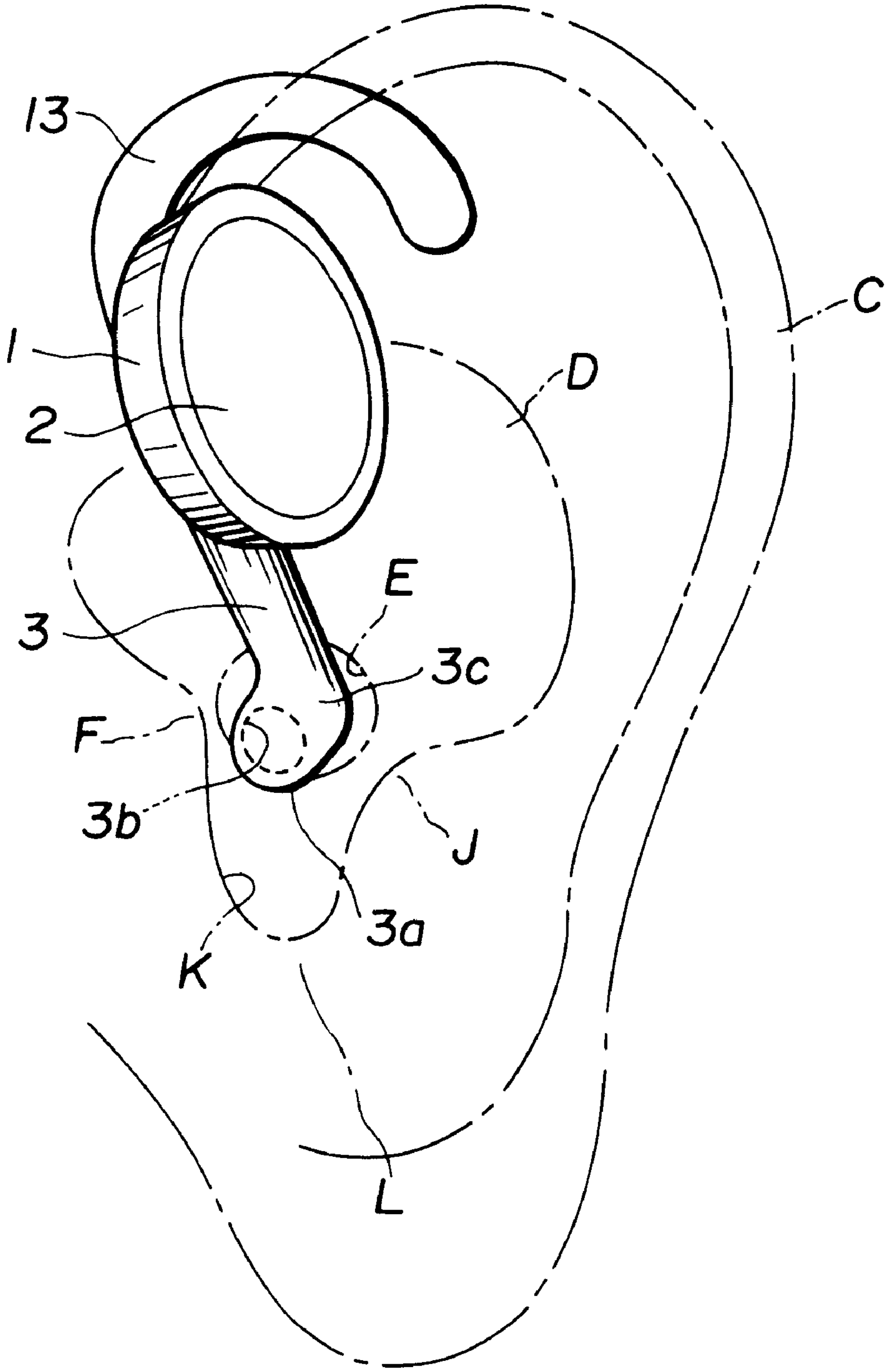
FIG. 7 is a perspective view showing still another example of the state in which the electro acoustic transducer arranged as an earphone device is attached to user's auricles.

The earphone device may also be constructed as shown in FIG. 7. An arm-shaped ear hanger 13, bent as a supporting member, is provided at the outward side of the cabinet 1. The ear hanger 13 is engaged and supported on the upper side of the outer lateral side of the auricle C. When ear hanger 13 is engaged with and supported by the auricle C, the distal side 3*a* of the sound guide tube 3 is inserted into the external auditory meatus E.

Figure 8:
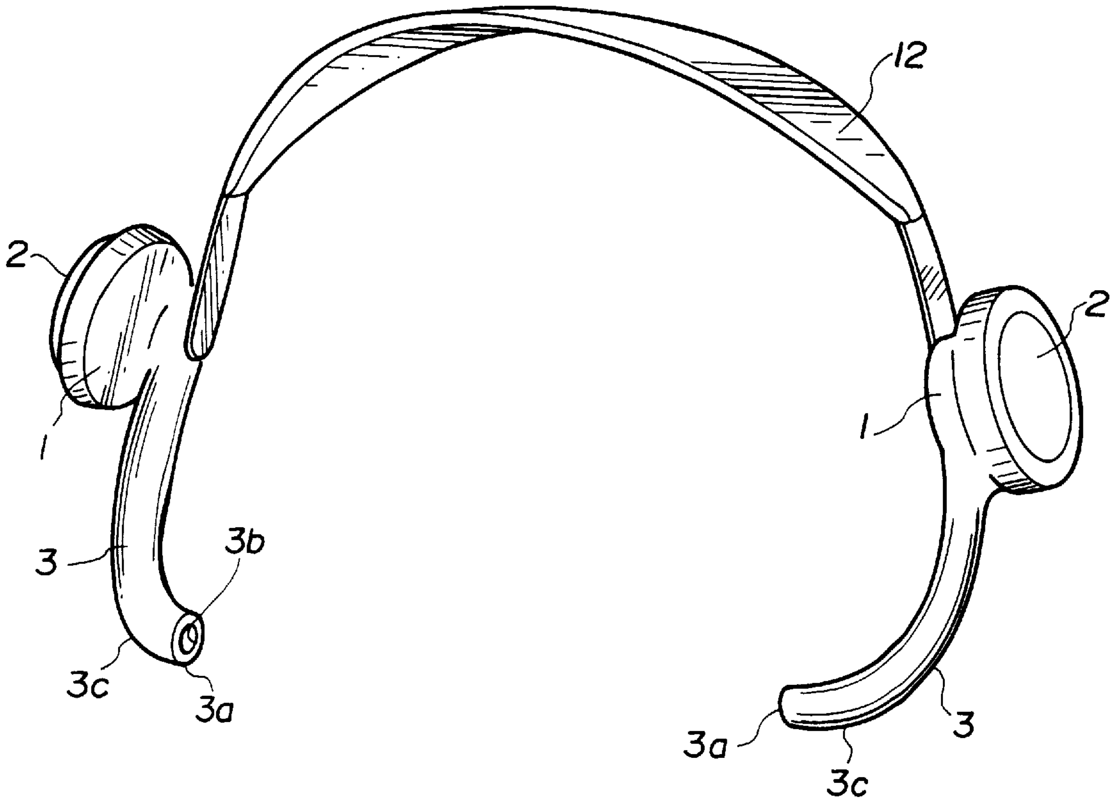
FIG. 8 is a perspective view showing the electro-acoustic transducer arranged as the headphone device.

The electro-acoustic transducer of the present invention may also be arranged for attachment to the user's head. Thus, as shown in FIG. 8, a pair of the above described earphone devices are attached to both sides of a hair band 12 adapted to conform substantially to the user's head. Such headphone device is used with the hairband 12 supported by the user's head and the distal sides of the sound guide tubes 3 of the earphone devices are inserted into external auditory meatuses of the user's left and right ears. The headphone device shown in FIG. 8 has a pair of sound reproducing units 2 to perform stereophonic reproduction.

Figure 9:
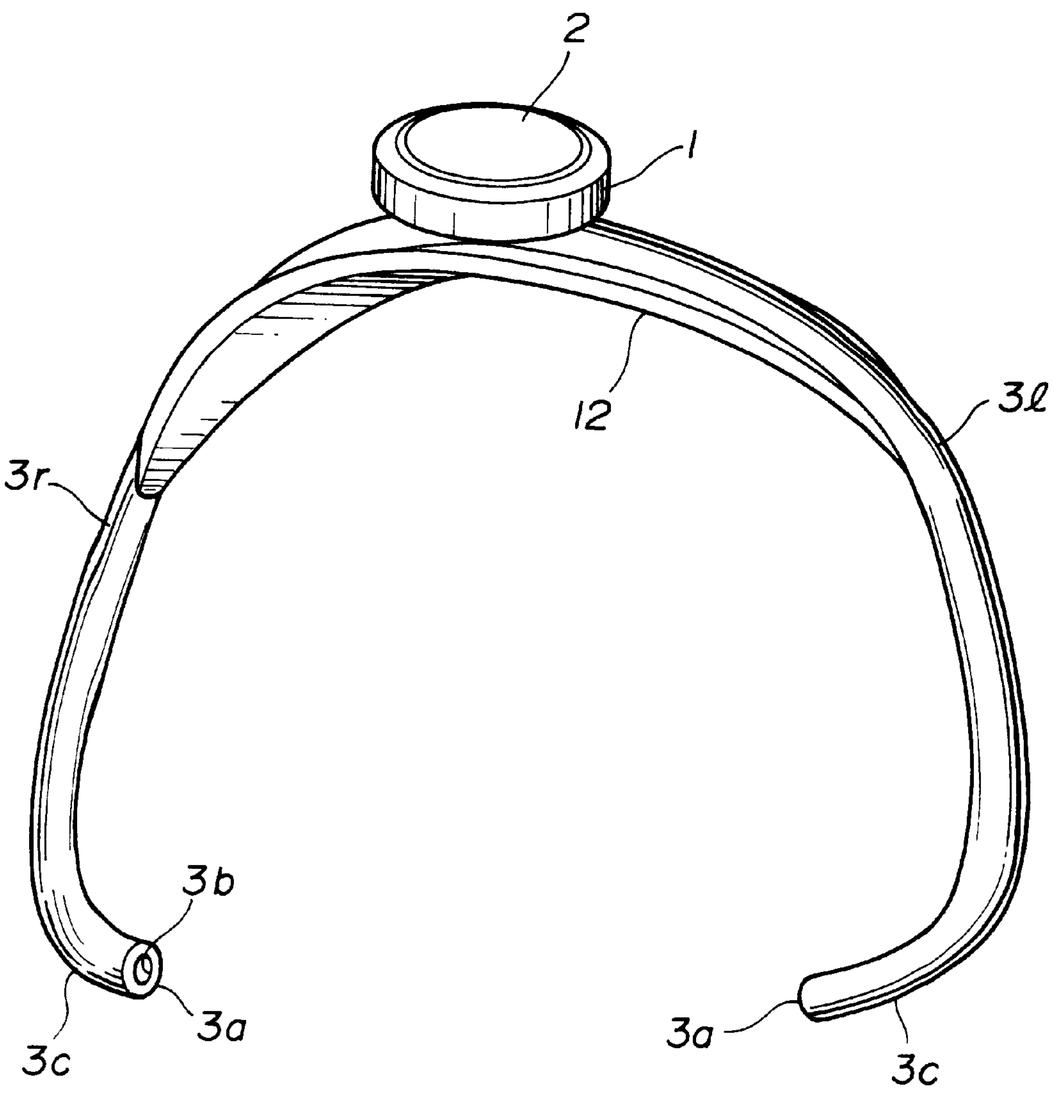
FIG. 9 is a perspective view showing still another example of construction of the electro-acoustic transducer.

The electro-acoustic transducer of the present invention may also be constructed as shown in FIG. 9. The cabinet 1 is provided on the hairband 12 and two sound guide tubes 31 and 3*r* for left and right ears are provided on the cabinet 1. The sound guide tubes 31 and 3*r* are adapted to project on both sides of the hairband 12. The hairband 12 is supported on the user's head and the distal sides 3*a* of the sound guide tubes 31 and 3*r* are inserted into the external auditory meatuses E of the user's left and right ears. The sound reproduced by the sound reproducing unit accommodated in and supported by the cabinet 1 is propagated through the sound guide tubes 31 and 3*r* to reach the external auditory meatuses E of the left and right ears.

Construction of Sound Reproducing System

Figure 10:
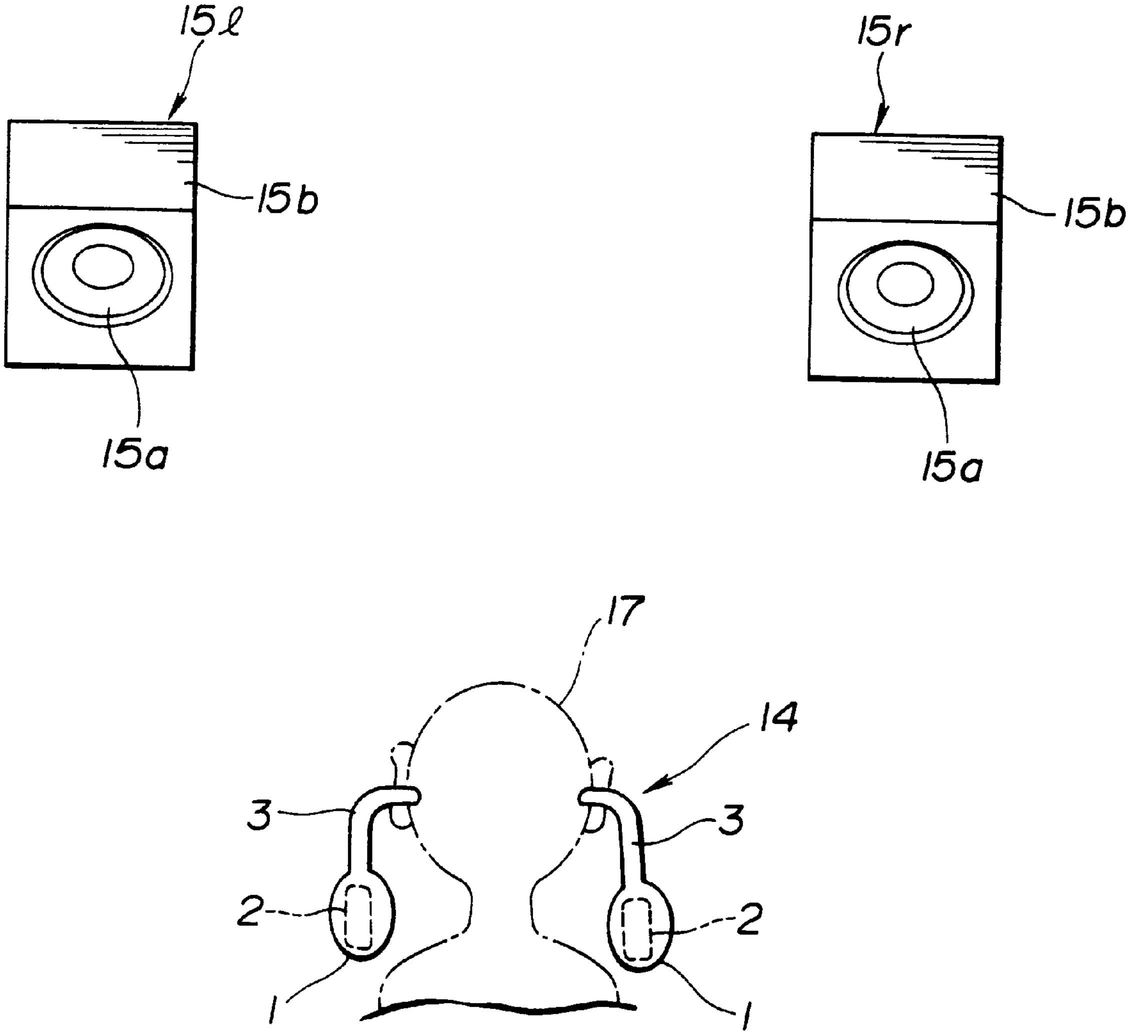
FIG. 10 is a diagrammatic perspective view showing the construction of the sound reproducing system of the present invention.

The sound reproducing system according to the present invention shown in FIG. 10 is comprised of a headphone device 14 of the type attached to-the user's auricles, which is provided with a pair of the earphone devices shown in FIG. 1 to constitute an electro-acoustic transducer. Left and right speaker devices 151 and 15*r* function as sound reproducing devices.

Each of the speaker devices 151 and 15*r* is provided with a speaker unit 15*a* having a magnetic circuit and a diaphragm and a speaker cabinet 15*b* accommodating and supporting the speaker unit 15*a* with the sound radiating side facing outwards. When the sound signals are supplied to the speaker devices 151 and 15*r*, these devices 151 and 15*r* convert the sound signals into vibrations of the diaphragm of the speaker unit 15*a* to reproduce the sound. The speaker units 151 and 15*r* are positioned on the left and right forward sides of the listener 17 with the sound radiating side facing the listener 17.

Figure 11:
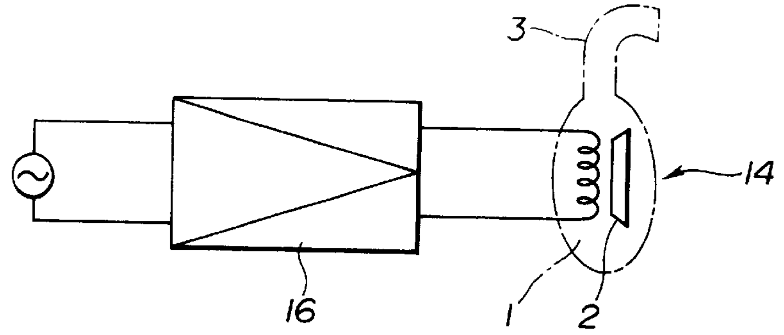
FIG. 11 is a circuit diagram showing the construction in the above sound reproducing system whereby the low frequency component of the acoustic signals may be supplied to the electroacoustic transducer.
Figure 12:
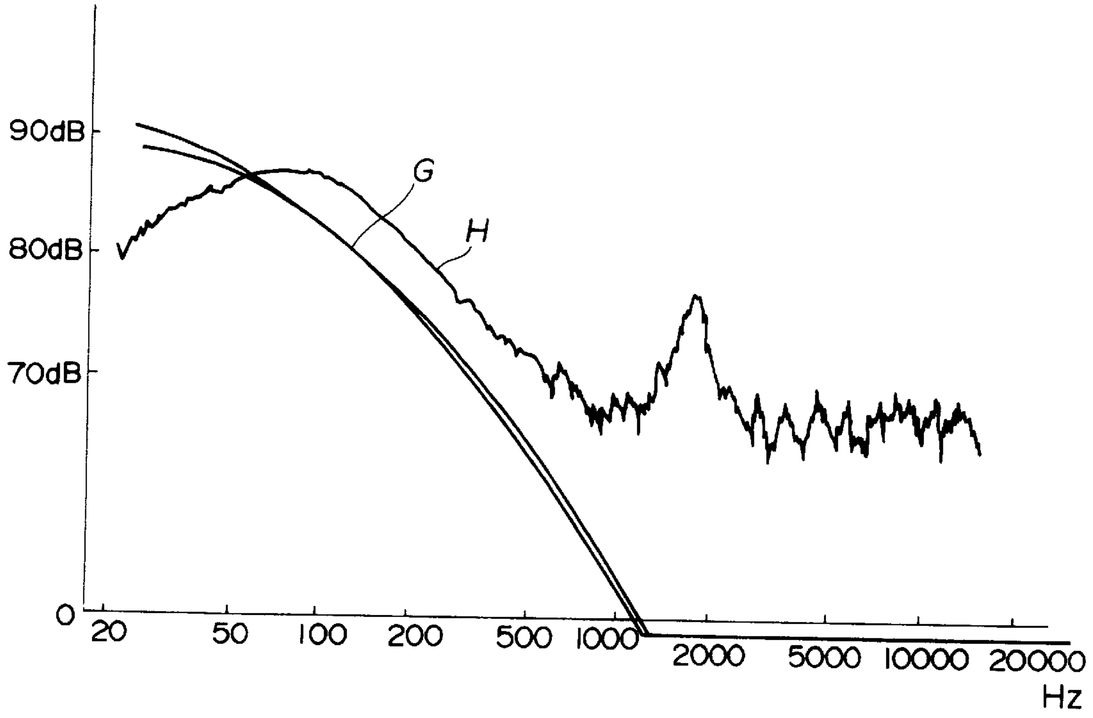
FIG. 12 is a chart showing frequency characteristics of the amplifier supplying the low frequency component of the acoustic signals to the electro-acoustic transducer shown in FIG. 11 and frequency characteristics of the reproduced sound of the transducer.

In order that only the low frequency component of the acoustic signals of the speaker devices 151 and 15*r* will be supplied to the headphone device 14, the above mentioned acoustic signals are supplied to the headphone device 14 via amplifier 16, as shown in FIG. 11. The amplification factor-frequency characteristics of the amplifier 16 are approximately zero at an area higher than about 1 kHz, as shown at G in FIG. 12. In the area below about 1 kHz, the amplification factor becomes higher.

The headphone device 14 supplied with the acoustic signals by way of the amplifier 16 performs sound reproduction with frequency characteristics in which the sound pressure is raised in the frequency range of 20 to 100 Hz.

With the above described sound reproducing system of the present invention, the acoustic signals are reproduced [as the sound] by the speaker devices 151 and 15*r*, while the low frequency component of the sound signals is reproduced by the headphone device. Since the headphone device 14 causes the reproduced sound to reach the tympanic membrane of the listener 17 without obstructing the external acoustic meatus E of the listener 17, the listener 17 may hear the sound reproduced by the speaker device 151 and 15*r* and the sound reproduced by the headphone device 14 simultaneously.

Hence, with the above described sound reproducing system, when the size of the speaker cabinet 15*b* or the speaker unit 15*a* constituting the speaker devices 151 and 15*r* is reduced and the sound reproduction by these speaker devices 151 and 15*r* in the low frequency range cannot be realized at a sufficient sound pressure, the sound reproduction in the low frequency range can be realized by the headphone device 14. That is, with the present sound reproducing system, the sound from the speaker devices 151 and 15*r* and the sound from the headphone device 14 cooperate to realize satisfactory sound reproduction over a wide frequency range including the low frequency range.

With the present sound reproducing system, the fixed position feel of the reproduced sound is approximately formed by the sound of the low to high frequency range reproduced by the speaker devices 151 and 15*r*. The sound of the low frequency range which is reproduced by the headphone device 14 does not essentially affect the fixed position feeling of the reproduced sound.

The amplifier 16 may also be so constructed that switching may be made between the amplification frequency characteristics emphasizing the above mentioned low frequency range and flatly amplifying the entire frequency range. When the amplification frequency characteristics of the amplifier 16 are substantially flat over the entire frequency range, the headphone device 14 reproduces the sound over the entire frequency range, so that satisfactory sound reproduction may be achieved without using the speaker devices 151 and 15*r*.

Figure 13:
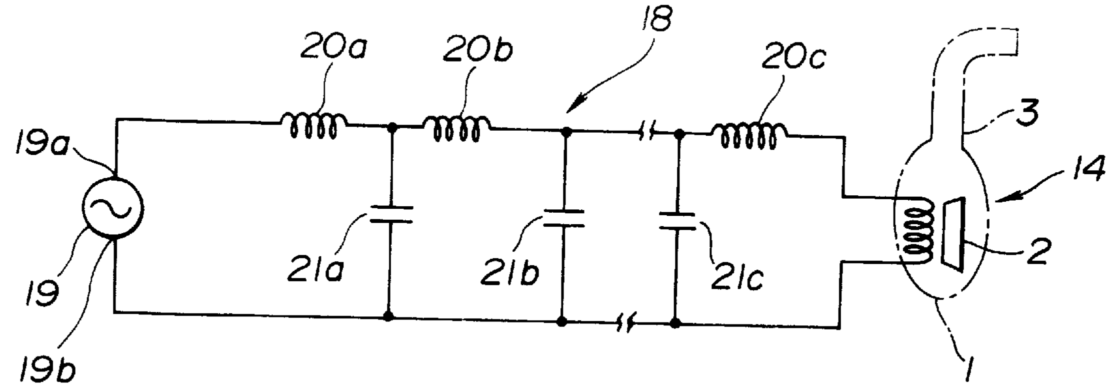
FIG. 13 is a circuit diagram showing another example of construction of supplying the low frequency component of the acoustic signals to the electro-acoustic transducer.

In order that only the low frequency component of the sound signal will be supplied to the headphone device 14, the sound signal may be supplied to the headphone device 14 via a so-called passive network type electrical circuit 18, as shown in FIG. 13. This passive network type electrical circuit 18 includes a plurality of coils 20*a*, 20*b*, 20*c* interposed between one output 19*a* of a signal source 19 and an input of the sound reproducing unit 2 of the headphone device 14. These coils 20*a*, 20*b*, 20*c* are connected in series with one another. Capacitors 21*a*, 21*b*, 21*c* are interposed between points between the coils 20*a*, 20*b*, 20*c* and the other output 19*b* of the signal source 19 connected to the other input of the sound reproducing unit 2.

The sound signals supplied to the headphone device 14 via passive network type electrical circuit 18 are supplied to the headphone device 14 after damping more strongly the higher frequency component. The degree of damping may be determined by suitably setting the inductance values of the coils 20*a*, 20*b*, 20*c* and the reactance values of the capacitors 21*a*, 21*b*, 21*c*. It may be represented by the proportion of the level of the sound signal at twice a given frequency damped with respect to the sound signals of a given frequency, as 6 dB/Oct or 12 dB/Oct.

The acoustic circuit for the headphone device 14 is shown in FIG. 2 wherein the equivalent mass Mb of the air in the sound guide tube is connected to the acoustic circuit for the sound reproducing unit 2. Therefore, the larger the equivalent mass Mb of the air within the sound guide tube 3, the lower is the resonance frequency of $f_0$ the headphone device 14. Thus a more satisfactory reproduction of the sound signal of the low frequency range may be realized by the headphone device 14.

The sound reproducing system according to the present invention is not limited to the construction in which sound reproduction for only the low frequency range may be made by the headphone device 14. The so-called surround sound may also be reproduced by the headphone device 14. That is, the sound signals supplied to the speaker devices 151 and 15*r* are supplied via so-called surround circuit to the headphone device 14. This surround circuit outputs the sound signal after predetermined delaying and damping.

With the above described sound reproducing system, the sound reproduced by the speaker devices 151 and 15*r* and the sound reproduced by the headphone device 14 cooperate to reproduce the sound with so-called concert-hall presence, that is, simultaneously with the reverberating and residual sound components.

Figure 14:
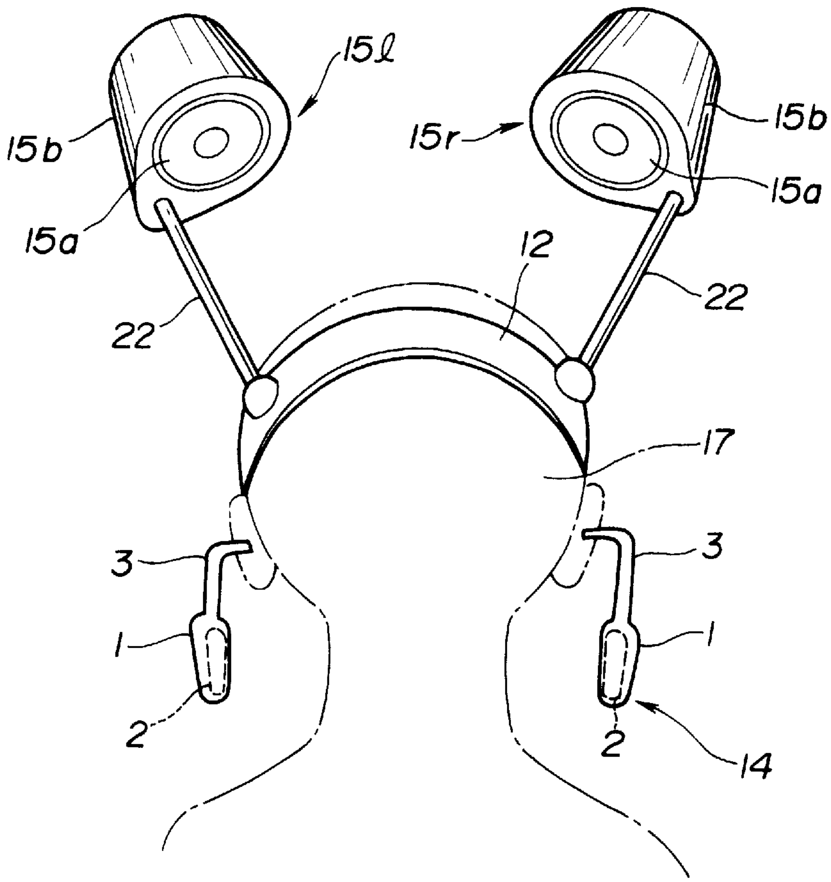
FIG. 14 is a perspective view showing the construction of supporting the sound reproducing apparatus of the sound reproducing system by the listener's head.

The sound reproducing system of the present invention may be constructed as shown in FIG. 14 wherein the speaker devices 151 and 15*r* are supported by the listener's head 17.

With the sound reproducing system, shown in FIG. 14 the speaker devices 151 and 15*r* are supported at the forward left and forward right sides of the listener 17, by the hairband 12 and a pair of speaker supporting arms 22 projectingly supported by the hairband 12. The sound radiating side faces the listener 17. The headphone device 14 is worn by the listener 17 as is the above mentioned sound reproducing system.

With the present sound reproducing system, the speaker devices 151 and 15*r* govern the stationary position feeling of the reproduced sound and are supported by the listener's head 17. The speaker devices 151 and 15*r* are moved to follow the listener's head when the listener 17 moves his head. Sound reproduction may thus be performed satisfactorily without changing the stationary position feeling.

Figure 15:
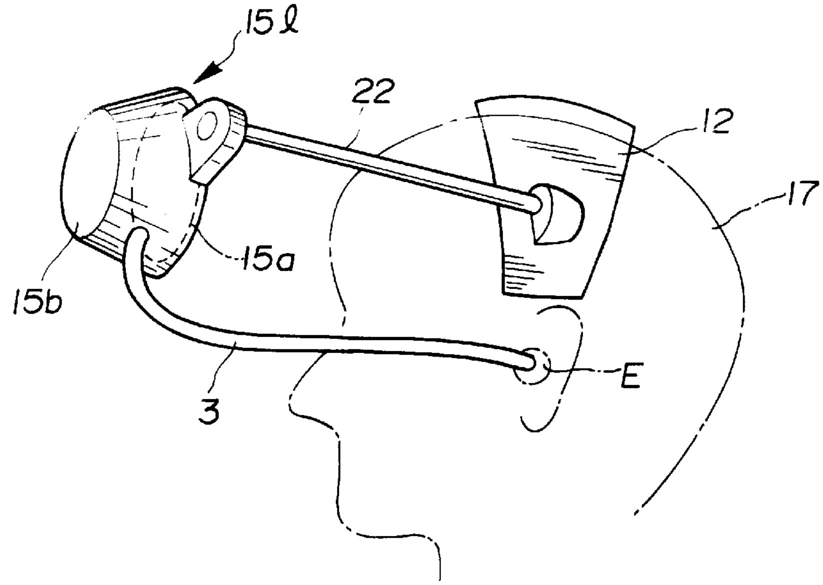
FIG. 15 is a side view showing the construction in which a sound guide tube is provided in the sound reproducing apparatus supported by the listener's head in the sound reproducing system.

On the other hand, when the speaker devices 151 and 15*r* are supported by the listener's head, the sound guide tube 3 may be provided on the speaker cabinet 15*b* of the speaker devices 151 and 15*r*, without using the headphone device 14, as shown in FIG. 15.

That is, with the present sound reproducing system, the sound guide tube 3, similar to that provided on the cabinet 1 of the headphone device 14, is provided on the speaker cabinet 15*b*. This sound guide tube 3 is so constructed that the sound radiated from the rear surface of the speaker cabinet 15*b* towards the inner side of the speaker cabinet 15*b* will be conducted outwards via sound guide opening 15*c* provided in the speaker cabinet 15*b*. The sound will be radiated via sound radiating opening 3*b* at the distal end 3*a* so as to reach the external auditory meatus E of the listener 17. The sound radiated by the speaker unit 15*a* towards the front side proves to be the sound reproduced by the sound reproducing device, while the sound radiated by the speaker unit 15*a* is equivalent to the sound reproduced by the electro-acoustic transducer.

The above described sound reproducing system is so designed that the resonance frequency in the speaker cabinet 15*b* and in the sound guide tube 3 becomes lower than the resonance frequency in the speaker unit 15*a*. The low frequency component of the sound radiated by the speaker unit 15*a* is conducted more efficiently in the sound guide tube 3. Thus, even if the sound pressure of the low frequency component of the reproduced sound radiated by the speaker devices 151 and 15*r* towards the front side is insufficient, the low range frequency component of the sound radiated towards the rear side of the speaker unit 15*a* is conducted by the sound guide tube 3 to the external auditory meatus E of the listener 17 to realize satisfactory sound reproduction.

When only the reproduction of the low frequency component of the sound is to be performed by the headphone device 14, the headphone device 14 may be replaced by a headphone device or an earphone device shown in FIGS. 5A to 9. Since the sound of the low frequency range does not affect the fixed position feeling, sound reproduction may be achieved satisfactorily when the sound of the low frequency range is supplied only to one ear. Another Construction of Electro-Acoustic Transducer of sound Reproducing System A variety of transducers constructed for satisfactorily reproducing the sound of the low frequency range may be used in addition to the above described headphone device 14, headphone device or earphone devices shown in FIGS. 5A to 9.

Figure 16:
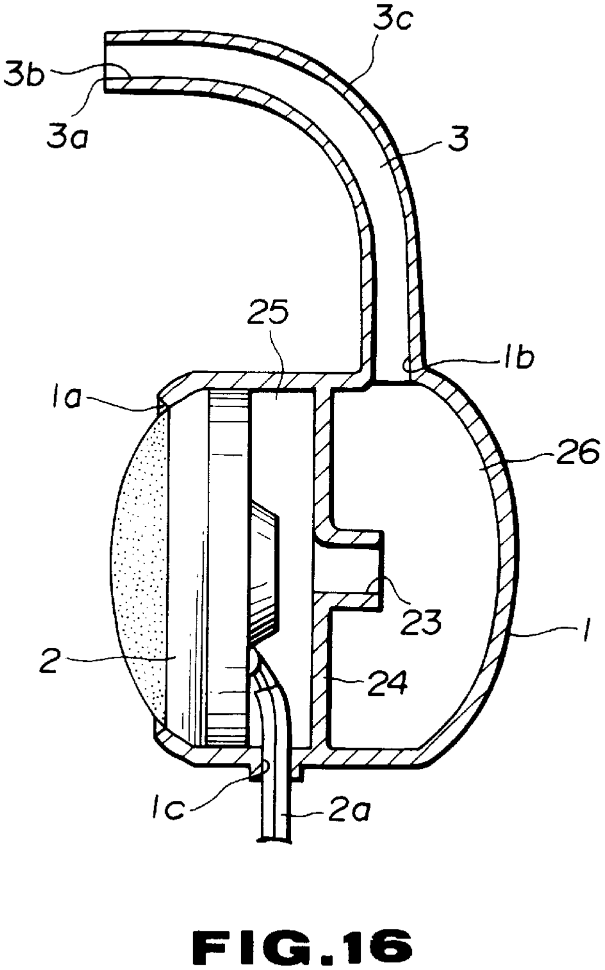
FIG. 16 is a cross-sectional view showing another example of construction of the electro-acoustic transducer in the sound reproducing system.

The earphone device constituting the headphone device 14 may be such a device as shown in FIG. 16. A partition wall 24 having a duct 23 in the cabinet 1 of the earphone device shown in FIG. 1 may be provided and this earphone device may be constructed as the so-called double bus ref type. With this earphone device, the inside of the cabinet 1 is divided by the partition wall 24 into a first air chamber 25 on the side of the sound reproducing unit 2 and a second air chamber 26 on the side of the sound guide opening 1*b* . These first and second air chambers 25, 26 communicate with each other by the above duct 23 provided in the partition wall 24.

The sound radiated towards the rear side of the sound reproducing unit 2 is radiated into the first air chamber 25 so as to be guided via duct 23 into the second air chamber 26. The sound guided into the second air chamber 26 is guided outwards via sound conducting opening 1*b* and the sound guide tube 3.

Figure 17:
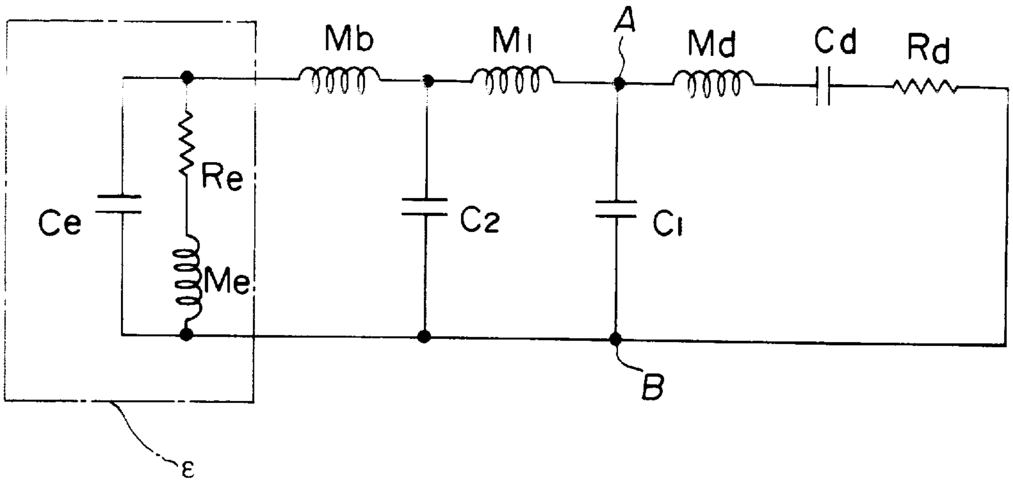
FIG. 17 is an equivalent acoustic circuit diagram showing acoustic characteristics of the electro-acoustic transducer shown in FIG. 16.

An equivalent acoustic circuit showing acoustic characteristics of the above described earphone device is shown din FIG. 17. The equivalent mass Md, compliance Cd and the acoustic resistance Rd of the sound reproducing unit 2 are connected in series and a compliance C1 in the first air chamber 25 is connected to the series circuit to form a closed loop. One of the junctions A between the equivalent mass Md, compliance Cd and the acoustic resistance Rd is connected to an acoustic circuit e of the external auditory meatus E by way of the air equivalent mass M1 in the duct 23 and the air equivalent mass Mb in the sound guide tube 3. The equivalent mass M1 and the equivalent mass Mb are connected, in series with each other. The other junction B between the equivalent mass Md, compliance Cd and the acoustic resistance Rd and the compliance C1 is connected to the acoustic circuit $\epsilon$ of the external auditory meatus E. A compliance C2 in the second air chamber 26 is interposed and connected between the junction between the equivalent mass M1 and the equivalent mass Mb and the other junction B.

In the acoustic circuit ϵ of the external auditory meatus E, the equivalent mass Me in the external auditory meatus E, compliance Ce and the acoustic resistance Re constitute a closed loop. The junction between the compliance Ce and the acoustic resistance Re is connected to the equivalent mass rib in the sound guide tube 3. The junction B between the compliance Ce and the equivalent mass Me is connected to the other junction.

With the above described earphone device, the resonance frequency $f_0$ of the earphone device may become lower. With a larger sum of the equivalent mass M1 and the equivalent mass Mb. That is, the resonance frequency $f_0$ may be made lower by an amount corresponding to the equivalent mass M1 of the air in the duct 23, as compared to the earphone device shown in FIG. 1 so that sound reproduction of the low frequency range may be performed satisfactorily.

Figure 18:
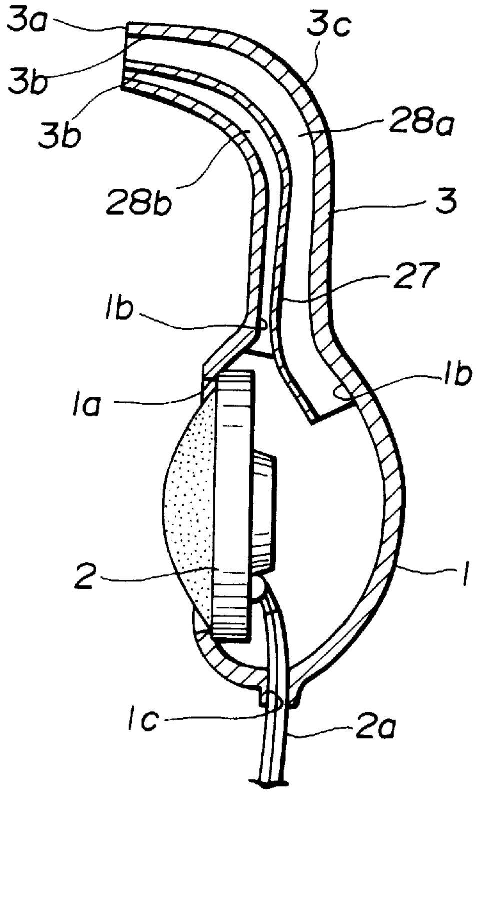
FIG. 18 is a cross-sectional view showing still another example of construction of the electro-acoustic transducer in the sound reproducing system.

With the earphone device constituting the headphone device 14, such transducer may be as shown in FIG. 18. The sound guide tube 3 of the earphone device shown in FIG. 1 is divided into plural sound guide sections 28*a*, 28*b* by a partition wall 27 formed along the axis of the sound guide tube 3.

The sound guide sections 28*a*, 28*b* defined by the partition wall 27 may have different inside diameters or lengths, while their equivalent masses in the sound guide sections 28*a*, 28*b* are approximately equal to one another. Hence, with the present earphone device, it becomes possible to prevent resonance from being produced along the length of the sound guide tube 3 to realize optimum sound reproduction in the low frequency range.

Figure 19:
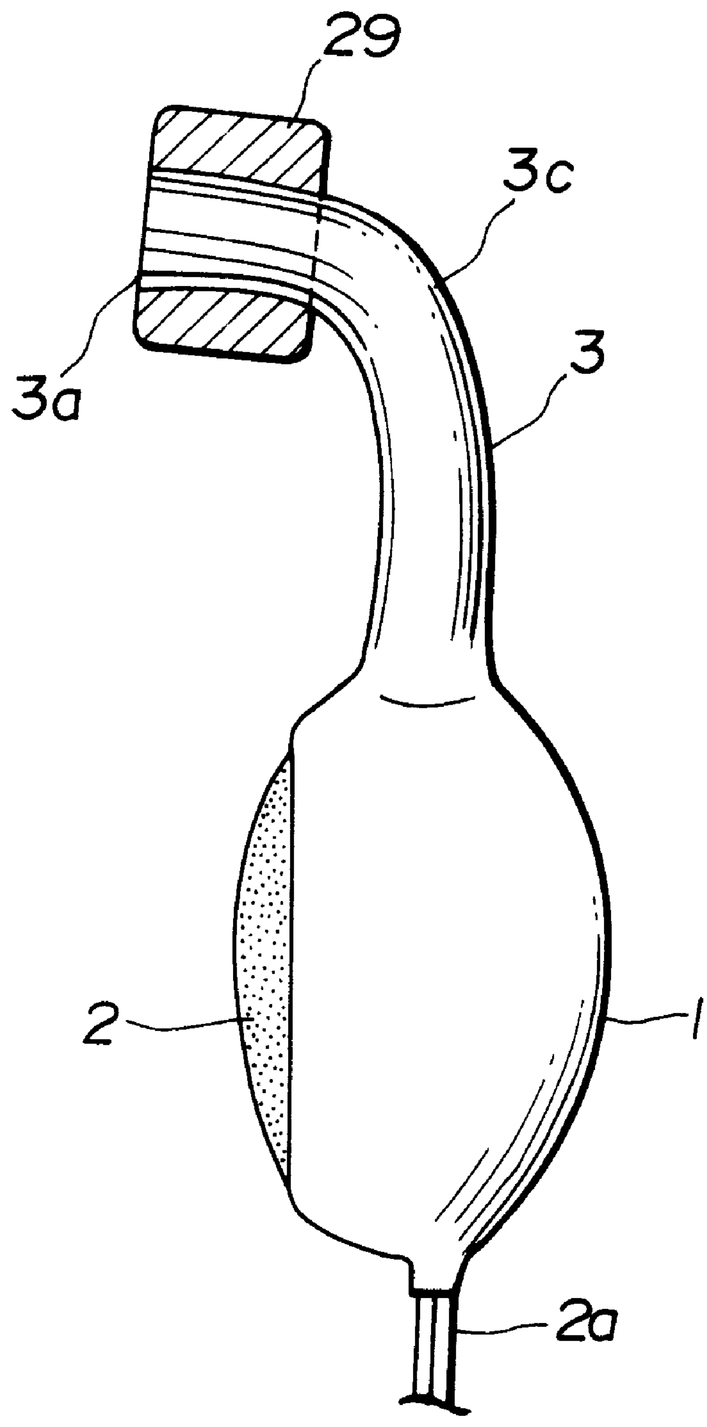
FIG. 19 is a side view showing another example of construction of sound guide tube of the electro-acoustic transducers of various types.

In the earphone device constituting the headphone device 14, a hermetic sealing member 29 formed of an air permeable material such as urethane may be provided for surrounding the outer peripheral surface of the distal side 3*c* of the sound guide tube 3, as shown in FIG. 19.

In such earphone device, the extent of hermetic sealing in the sound guide tube 3 and the external auditory meatus E is improved to increase the sound pressure of the reproduced sound in the low frequency range.

Since the sealing member 29 exhibits air permeability, it does not obstruct the hearing of the sound reproduced by the speaker devices 151 and 15*r* or the exterior sound. The sealing member 29 may be made detachable with respect to the sound guide tube 3.

Another Construction of Sound Reproducing Device of Sound Reproducing System

With the sound reproducing system constituting the sound reproducing system of the present invention, headphone devices may be designed for performing sound reproduction over the entire frequency range, from the low to the high range along with the above mentioned speaker devices 151 and 15*r*.

Figure 20:
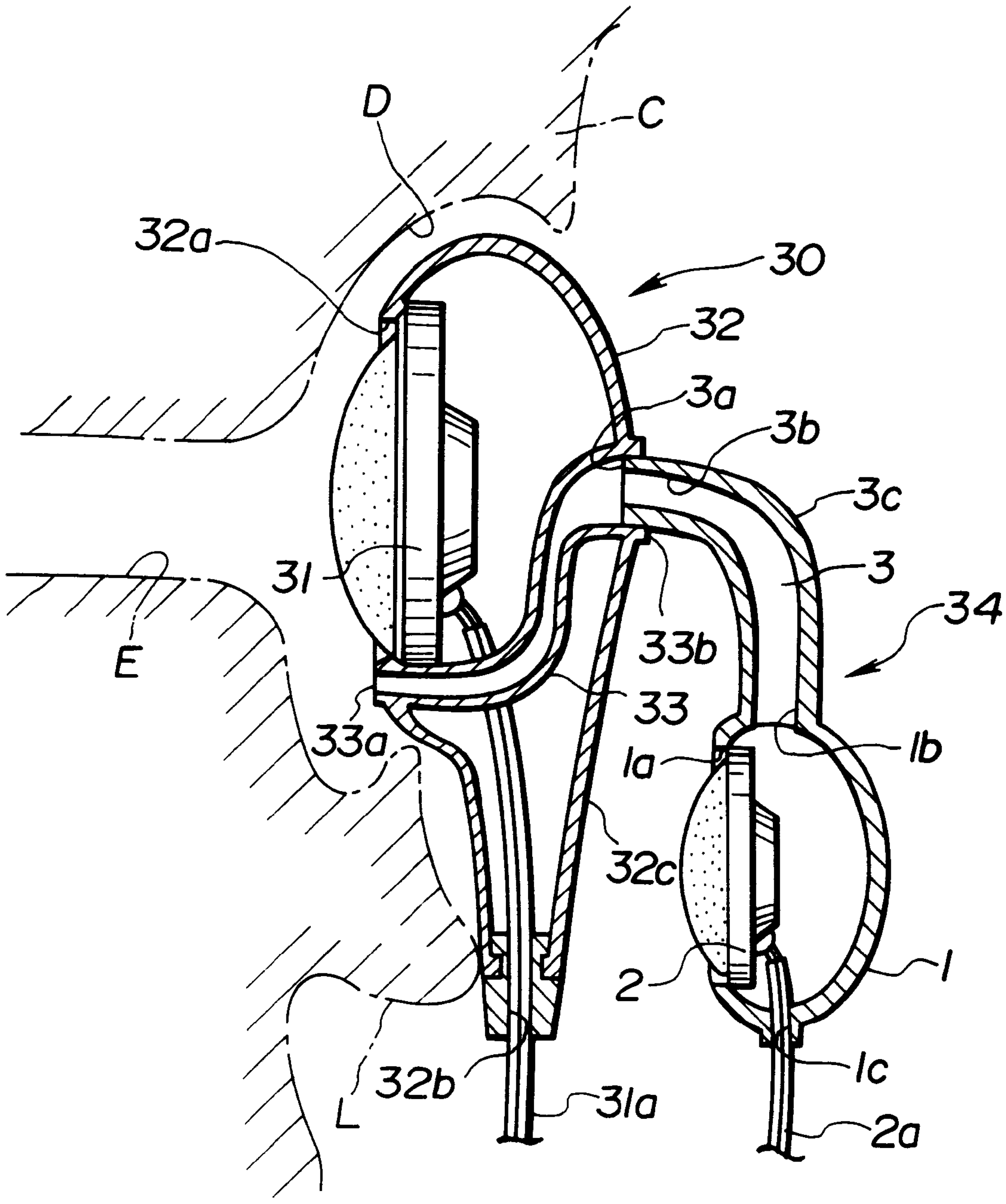
FIG. 20 is a cross-sectional view showing the construction using the headphone device attached to the user's auricle as the sound reproducing device in the above sound reproducing system.

Thus, as shown in FIG. 20, this sound reproducing system is comprised of a headphone device of the type attached to the user's auricle, which is supplied with acoustic signals to reproduce the sound. An electro-acoustic transducer 34 may be adapted for reproducing at least the low frequency component of the acoustic signals supplied by means of the amplifier 16 or the passive network 18. The electro-acoustic transducer 34, the earphone devices shown in FIGS. 1, 5A to 9, 16 or 18, or a headphone device making use of a pair of such earphone devices, may be used.

The headphone device attached to the user's auricles 30 is adapted for supporting a pair of sound reproducing units 31, adapted for converting acoustic signals into sound, in a confronting relation at the inlets to both external auditory meatuses E. The sound reproducing units 31 are accommodated in and supported by a headphone cabinet 32, as shown in FIG. 20, with the sound radiating side facing outwards by means of the sound radiating opening 32*a*. This headphone cabinet 32 is accommodated in the cavity of the concha D, with the sound radiating side of the sound reproducing unit 31 facing the inlet to the external auditory meatus E, and is supported by the tragus add the antitragus. A feeder 31*a* supplying the sound signal to the sound reproducing unit 31 is taken out by way of a cord guide section 32*b* extended from the headphone cabinet 32 and by way of a feeder outlet 32*c* provided at the foremost part of the cord guide section 32*c*.

The headphone cabinet 32 is provided with a sound guide extension tube 33 for establishing communication between the vicinity of the periphery of the sound reproducing unit 31, which is the sound radiating side of the sound reproducing unit 31, and the back side of the headphone cabinet 32 facing the sound radiating side. The sound, guide extension tube 33 is formed as a tube opened at both ends and made integral with the headphone cabinet 32. One opening end 33*a* faces the front side of the periphery of the sound reproducing unit 31 and the other opening end 33*b* faces the rear side from the center on the rear surface of the headphone cabinet 32.

The distal end 3*a* of the sound guide tube 3 of the electroacoustic transducer 34 may be detachably inserted and engaged into the other opening end 33*b* of the sound guide extension tube 33. The sound radiated from the rear surface of the sound reproducing unit 2 of the electro-acoustic transducer 34 into the inside of the cabinet 1 of the electro-acoustic transducer 34 is conducted into the inside of the sound guide extension tube 33 by way of the sound guide tube 3, the sound radiating opening 3*b* and the other opening end 33*b* of the sound guide extension tube 33. The sound thus conducted into the sound guide extension tube 33 is propagated in the extension tube 33 so as to be radiated at one opening end 33*a* facing the front side. The one opening end 33*a* of the sound guide extension tube 33 faces the inlet of the external auditory meatus E, as does the acoustic transducer unit 31 so that the sound radiated from the opening end 33*a* reaches the inside of the external auditory meatus E.

With the above described sound reproducing system, the sound is reproduced over the entire frequency range. Even if the low frequency component of the sound reproduced by the headphone device attached to the user's auricle 30 has an insufficient sound pressure, the sound of the low frequency range is reproduced by the electro-acoustic transducer 34 to reach the external auditory meatus E. The sound reproduced by the headphone device attached to the user's auricle 30 and the sound reproduced by the electro-acoustic transducer 34 cooperate with each other to effect satisfactory sound reproduction.

On the other hand, when employing the headphone device as the sound reproducing apparatus, the headphone device of the so-called hermetically sealed headphone device may be employed.

Figure 21:
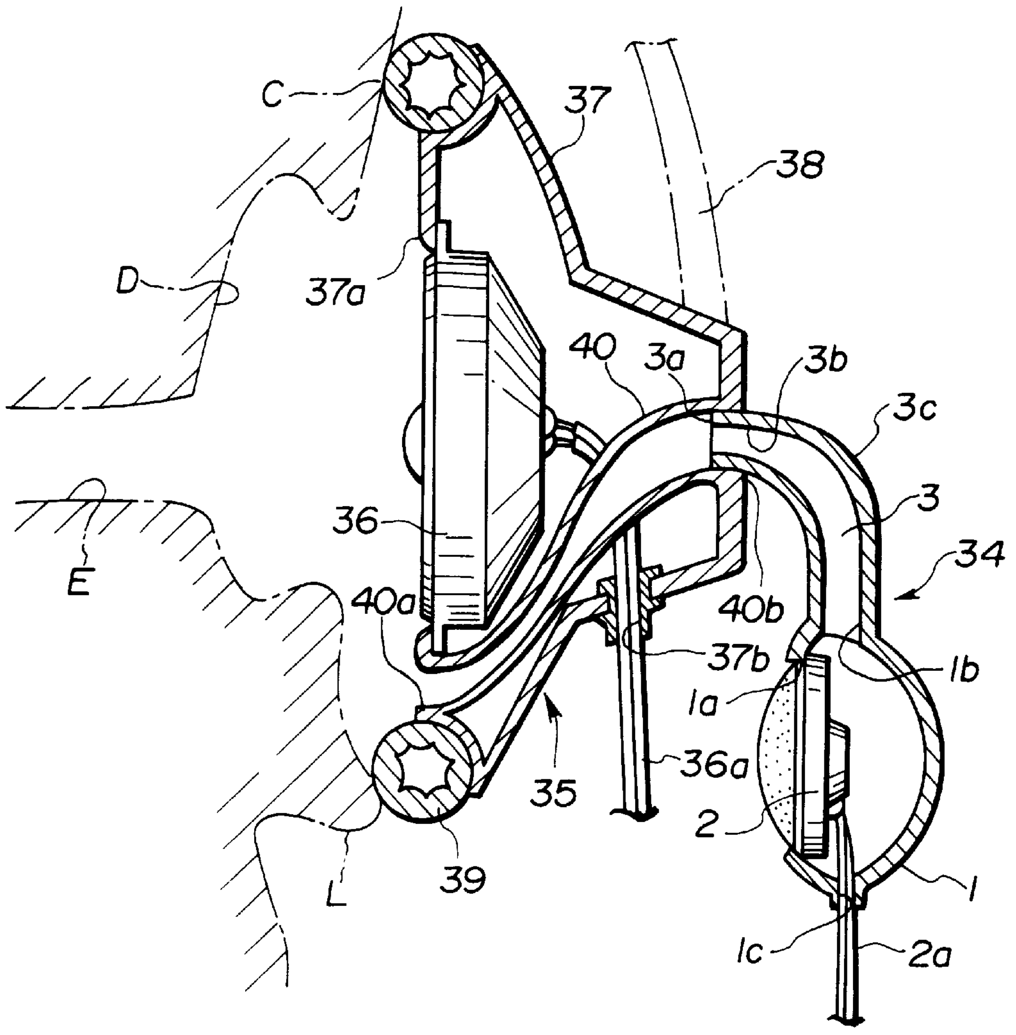
FIG. 21 is a cross-sectional view showing the construction of the hermetically sealed headphone device used as the sound reproducing apparatus of the sound reproducing system.

The head attachment type headphone device 35 is constructed so that a pair of sound reproducing units 36 for converting acoustic signals into sound are supported in a confronting relation to the entrance to both external acoustic meatuses E, as shown in FIG. 21. The sound reproducing unit 36 is accommodated in the associated headphone cabinet 37, with the sound radiating surface facing outwards by way of the sound radiating opening 37*a*. These headphone cabinets 37 are attached to both ends of the headband 38 and, with the headband 38, are supported by the listener's head.

The headphone cabinets 37 are supported in abutment with the auricles C so that the sound radiating surface of the sound reproducing unit 36 faces the inlet to the external acoustic meatus E. On the perimeter of the headphone cabinet 37 abutting on the auricle C is mounted an annular buffer member 39 of urethane or rubber. The feeder 36*a* for supplying acoustic signals to the sound reproducing unit 36 is extracted outwards by a feeder outlet 37*b* provided at the headphone cabinet 37.

The headphone cabinet 37 is provided with a sound guide extension tube 40 for establishing communication between the perimeter of the sound reproducing unit 36 on the front side and the rear surface of the headphone cabinet 37. The sound guide extension tube 40 is formed in the headphone cabinet 37 as a tube which is opened on both sides and formed integrally with the headphone cabinet 37. One opening end 40*a* faces forward from the periphery of the sound reproducing unit 36 and the other opening end 40*b* faces rearward from the center rear surface of the headphone cabinet 37.

The other opening end 40*b* of the sound guide extension tube 40 is so formed that the distal end 3*a* of the sound guide end 3 of the electro-acoustic transducer 34 may be detachably inserted and engaged therein. The sound radiated from the rear side of the sound reproducing unit 2 of the electro-acoustic transducer 34 is adapted to be transmitted into the sound guide extension tube 40 by way of the sound guide tube 3, the sound radiating opening 3*b* and the other opening end 40*b* of the sound guide extension tube 40. The sound transmitted into the sound guide extension tube 40 is propagated within the sound guide extension tube 40 so as to be radiated at the one opening end 40*a* facing the front side. The one opening end 33*a* of the sound guide extension tube 40 faces the inlet to the external auditory meatus E, as does the acoustic transducer unit 36 of the hermetically sealed headphone device 35. The sound radiated from one opening end 40*a* may thus reach the external acoustic meatus E.

With the above described sound reproducing system, the sound may be reproduced over the full frequency range by the above mentioned hermetically sealed headphone device 35. Even if the low frequency component of the sound reproduced by this hermetically sealed headphone device 35 has an insufficient sound pressure, the sound of the low frequency range is reproduced by the electro-acoustic transducer 34 so as to reach the external auditory meatus E. The sound reproduced by the hermetically sealed headphone device 35 and the sound reproduced by the electro-acoustic transducer 34 cooperate with each other to effect satisfactory sound reproduction.

EFFECT OF THE INVENTION

With the above described electro-acoustic transducer of the present invention, the sound guide tube having a smaller diameter than the external auditory meatus, at least at the sound radiating end, is inserted into the external auditory meatus. Thus, it becomes possible for the electroacoustic transducer to conduct the sound through the external auditory meatus without obstructing the external auditory meatus.

Hence, with the present electro-acoustic transducer, no standing waves are produced in the space between the tympanic membrane of the listener and the transducer unit. The extraneous sound may be propagated into the external auditory meatus by way of the space between the inner wall of the external auditory meatus and the outer periphery of the sound guide tube.

Thus the present invention may provide an electro-acoustic transducer which may be applied advantageously to, for example, an earphone device or a headphone device, and which may reproduce the sound without an oppressed feeling or a stationary position feeling.

In addition, the electro-acoustic transducer is supplied with acoustic signals to reproduce the sound by a sound reproducing device, and at least the low frequency component of the acoustic signal supplied to the sound reproducing device is converted into sound. The sound is radiated into the external auditory meatus, without plugging the external auditory meatus, by means of a sound guide tube of a smaller diameter than the external auditory meatus. The sound radiated from the electro-acoustic transducer unit accommodated in the cabinet may be conducted toward the outside of the cabinet and at least the sound radiating side may be inserted into the external auditory meatus.

Hence, with the present sound reproducing system, both the sound reproduced by the sound reproducing device and the sound reproduced by the sound reproducing unit of the headphone device may be heard simultaneously.

Thus, even if the low frequency component of the sound reproduced by the sound reproducing device has an insufficient sound pressure, this sound may reach the external auditory meatus E. Thus the sound reproduced by the hermetically sealed headphone device 35 and the sound reproduced by the electro acoustic transducer cooperate to result in satisfactory sound reproduction.

With the above described electro-acoustic transducer of the present invention, the sound guide tube for conducting the sound radiated from the electro-acoustic transducer unit accommodated in the cabinet has at least a sound radiating with a smaller diameter than the external auditory meatus so that the sound radiating end may be inserted into the external auditory meatus. Thus it is possible with the present electric-acoustic transducer to conduct the sound into the external auditory miatus without occluding it.

Thus, with the present electro-acoustic transducer, no standing waves are produced between the listener's tympanic membrane and the electro-acoustic transducer unit, while extraneous sound may be propagated between the inner wall of the external auditory meatus and the outer peripheral surface of the sound guide tube.

Thus the present invention provides an electro-acoustic transducer which may be advantageously applied to, for example, an earphone device or a headphone device. Also, the sound may be reproduced without causing an oppressed feeling or a stationary position feeling, that is a feeling as if the sound source were situated stationarily within the listener's head.

With the sound reproducing system according to the present invention, the sound reproducing device is adapted to be supplied with acoustic signals and to transduce the acoustic signals into sound for reproduction thereof. The electro-acoustic transducer is adapted to transduce at least the low frequency component of the acoustic signals supplied into the sound reproducing device into sound. The electro-acoustic transducer radiates the sound into the external auditory meatus without occluding it by means of a sound guide tube which has a smaller diameter than the external auditory meatus. The sound is radiated from the electro-acoustic unit accommodated in the cabinet towards the outside of the cabinet and permits at least the sound radiating end to be inserted into the external auditory meatus.

Hence, with the present sound reproducing system both the sound reproduced by the sound reproducing device and the sound reproduced by the sound reproducing unit of the headphone device may be heard simultaneously.

Therefore, even if the low frequency component of the sound reproduced by the sound reproducing device has an insufficient sound pressure, this sound cooperates with the sound reproduced by the electro-acoustic transducer to achieve satisfactory sound reproduction.

It is noted that, since the stationary position feeling of the reproduced sound is formed by the medium to high frequency range reproduced by the sound reproducing device, the stationary position feeling is hardly affected by the sound in the low frequency range even if the sound in the low frequency range is radiated into the external auditory meatus.

Thus the present invention provides a sound reproducing system in which the sound may be reproduced satisfactorily over a wide frequency range, encompassing the low frequency range, without increasing the size of the system or the inconvenience to the neighbors.

What is claimed is:

1. An electro-acoustic apparatus, comprising:

an electro-acoustic transducer accommodated in a cabinet; and a sound guide tube for conducting the sound from the electro-acoustic transducer unit out of said cabinet;

said sound guide tube having a smaller diameter than an external acoustic meatus to allow at least a sound radiating end of the sound guide tube to be inserted into the external acoustic meatus;

said electro-acoustic apparatus further comprising supporting means for supporting one of said transducer or said sound guide tube so that the sound radiating end of said sound guide tube is at a predetermined position within the external acoustic meatus;

wherein said cabinet is formed for enclosing the rear side of said electro-acoustic transducer unit and not a sound radiating side of said electro-acoustic transducer, said sound guide tube being L-shaped and having an end opposite to said sound radiating end connected to a sound conducting opening provided on a lateral side of said cabinet.

2. The electro-acoustic transducer according to claim 1 wherein said supporting means comprises at least one projection provided at the distal side of said sound conducting tube and adapted to be engaged with an auricular recess.

3. The electro-acoustic transducer according to claim 1 wherein said supporting means comprises a toroidal member provided at the distal end of said sound guide tube and adapted for being held in the cavity of the concha.

4. The electro-acoustic transducer according to claim 1 wherein said supporting means comprises an ear hanger provided outside the cabinet and engaged with the upper side of the outer periphery of said cabinet.

5. The electro-acoustic transducer according to claim 1 wherein said supporting means comprises a head band.

6. The electro-acoustic transducer according to claim 5 wherein said cabinet is provided at an upper end portion of said head band and a pair of said sound guide tubes are provided at said cabinet.

7. The electro-acoustic transducer according to claim 1 wherein acoustic signals supplied to said transducer unit are supplied thereto by way of a compensation circuit for compensating frequency resonance peaks generated in said transducer unit.

8. A sound reproducing system, comprising:

a sound reproducing apparatus supplied with acoustic signals; and an electro-acoustic transducer unit including an electro-acoustic transducer accommodated in a cabinet, and a sound guide tube for conducting the sound from the electro-acoustic transducer out of said cabinet;

said sound guide tube having at least a sound radiating end with a smaller diameter than an external auditory meatus to permit said sound radiating end to be inserted into the external auditory meatus and to define a space between said sound radiating end of said sound guide tube and said external auditory meatus, said space for allowing surrounding noises to enter the external auditory meatus and be heard by a user;

said electro-acoustic transducer reproducing at least a low-frequency component of a frequency range of the acoustic signals of the sound reproduced by said sound reproducing apparatus.

9. The sound reproducing system according to claim 8, further comprising means for supplying only said low frequency component of the acoustic signals to said electro-acoustic transducer.

10. The system according to claim 6 further comprising amplifier means for amplifying the low frequency component of the acoustic signal supplied to said sound reproducing apparatus.

11. The system according to claim 8 wherein said amplifier means comprises a passive network electric circuit.

12. An electro-acoustic apparatus comprising:

an electro-acoustic transducer for receiving electrical signals and for generating acoustic signals;

a cabinet for enclosing a rear side of said electro-acoustic transducer and wherein a sound radiating side of said electro-acoustic transducer is not enclosed by said cabinet;

a sound guide tube connected to said cabinet and having a sound radiating end inserted into an external acoustic meatus of a user for conducting more of a low frequency component than higher frequency components of said acoustic signals to said external acoustic meatus;

wherein an inside diameter of said external acoustic meatus is greater than an outside diameter of said sound radiating end thereby defining a space between said external acoustic meatus and said outside diameter of said sound guide tube for allowing surrounding noises to enter said space and be heard by said user whereby said external acoustic meatus is not completely obstructed by said electro-acoustic apparatus.

13. The electro-acoustic apparatus according to claim 12, wherein said acoustic signals generated by said electro-acoustic transducer are at least contained within a certain bandwidth and secondary acoustic signals received in said external acoustic meatus have a bandwidth which is at least partially outside of said certain bandwidth.

14. The electro-acoustic apparatus according to claim 13, wherein said secondary acoustic signals are generated by at least a second electro-acoustic transducer located remote from said electro-acoustic transducer.

15. The electro-acoustic apparatus according to claim 13, wherein said secondary acoustic signals are generated by at least a second electro-acoustic transducer attached to an ear of said user, said second electro-acoustic transducer having a sound radiating side which directs said external acoustic signals into said external acoustic meatus.

16. The electro-acoustic apparatus according to claim 12, wherein said sound guide tube is divided into a plurality of tubes with each one of said plurality of tubes defining a separate passage from said electro-acoustic transducer to said external auditory meatus.

17. An electro-acoustic apparatus, comprising:

an electro-acoustic transducer having a sound radiating side and a rear side opposite said sound radiating side, said electro-acoustic transducer for converting electrical signals into acoustic signals;

a cabinet for enclosing said rear side of said electro-acoustic transducer but not said sound radiating side;

a sound guide tube having one end connected to said cabinet and another end for insertion within an external acoustic meatus of a user;

wherein an inside diameter of said sound guide tube is sized so that more of a low frequency component of said acoustic signals is conducted in said sound guide tube than higher frequency components of said acoustic signals.

18. The electro-acoustic apparatus as set forth in claim 17, wherein an outside diameter of said sound guide tube is smaller than an inside diameter of said external acoustic meatus and said sound guide tube is spaced from said external acoustic meatus to allow the passage of acoustic signals from a secondary source through said external acoustic meatus.

19. The electro-acoustic apparatus as set forth in claim 17, further comprising filtering means for filtering out said higher frequency components and wherein said sound guide tube conducts only said low frequency component.

20. An electro-acoustic apparatus, comprising:

an electro-acoustic transducer having a sound radiating side and a rear side opposite said sound radiating side, said electro-acoustic transducer for converting electrical signals into acoustic signals;

a cabinet for enclosing said rear side of said electro-acoustic transducer but not said sound radiating side;

a sound guide tube having one end connected to said cabinet and another end for insertion within an external acoustic meatus of a user;

wherein an outside diameter of said sound guide tube is smaller than an inside diameter of said external acoustic meatus and said another end of said sound guide tube is spaced from said external acoustic meatus to allow the passage of acoustic signals from a secondary source through said external acoustic meatus.

21. The electro-acoustic apparatus as set forth in claim 20, wherein an inside diameter of said sound guide tube is sized so that more of a low frequency component of said acoustic signals is conducted in said sound guide tube than higher frequency components of said acoustic signals.

22. The electro-acoustic apparatus as set forth in claim 21, further comprising means for filtering out said higher frequency components and wherein said sound guide tube conducts only said low frequency.

* * * * *

UNITED STATES PATENT AND TRADEMARK OFFICE

CERTIFICATE OF CORRECTION

PATENT NO. : 6,307,943 B1
DATED : October 23, 2001
INVENTOR(S) : Yamagishi

It is certified that error appears in the above-identified patent and that said Letters Patent is hereby corrected as shown below:

Column 15,
Line 42, replace "the distal side" with -- said sound radiating end --.
Line 46, replace "the distal end" with -- said sound radiating end --.

Signed and Sealed this

Twenty-ninth Day of July, 2003

JAMES E. ROGAN
*Director of the United States Patent and Trademark Office*